United States Patent [19]
Burt et al.

[11] Patent Number: 5,521,306
[45] Date of Patent: May 28, 1996

[54] PROCESSES FOR THE PREPARATION OF HYDROXYGALLIUM PHTHALOCYANINE

[75] Inventors: Richard A. Burt, Oakville; Cheng-Kuo Hsiao; Dasarao Murti, both of Mississauga; Roger E. Gaynor, Oakville; Barkev Keoshkerian, Thornhill; James D. Mayo, Toronto; George Liebermann, Mississauga, all of Canada

[73] Assignee: Xerox Corporation, Stamford, Conn.

[21] Appl. No.: 233,834

[22] Filed: Apr. 26, 1994

[51] Int. Cl.⁶ ............................................. C09B 67/50
[52] U.S. Cl. ...................... 540/141; 540/139; 540/140; 540/142; 540/143
[58] Field of Search .................................. 540/139, 140, 540/141, 142, 143

[56] References Cited

FOREIGN PATENT DOCUMENTS

| | | |
|---|---|---|
| 52-63007 | 3/1977 | Japan . |
| 1221459 | 9/1989 | Japan . |

OTHER PUBLICATIONS

Bull. Soc. Chim. Fr., 23 (1962), D. Colaitis.
J. Chem. Soc., 1717, 1936, P. A. Barrett et al.
Inorg. Chem., 25, 3972, 1986, C. Ercolani et al.
Russ. J. Phys. Chem. (Engl. Transl.), 41, 251, 1967, I. S. Kirin et al.
Inorg. Chem. 12, 930, 1973, W. R. Bennett et al.

*Primary Examiner*—Mukund J. Shah
*Assistant Examiner*—Pavanaram K. Sripada
*Attorney, Agent, or Firm*—E. O. Palazzo

[57] ABSTRACT

A process for the preparation of Type V hydroxygallium phthalocyanine which comprises the in situ formation of an alkoxy-bridged gallium phthalocyanine dimer, hydrolyzing said alkoxy-bridged gallium phthalocyanine dimer to hydroxygallium phthalocyanine, and subsequently converting the hydroxygallium phthalocyanine product obtained to Type V hydroxygallium phthalocyanine.

34 Claims, 9 Drawing Sheets

PROCESSES FOR THE PREPARATION OF HYDROXYGALLIUM PHTHALOCYANINE

BACKGROUND OF THE INVENTION

This invention is generally directed to hydroxygallium phthalocyanines and photoconductive imaging members thereof, and more specifically the present invention is directed to processes for the preparation of hydroxygallium phthalocyanines from alkoxy-bridged gallium phthalocyanine dimers, and layered photoconductive members comprised of the aforementioned hydroxygallium phthalocyanine. The present invention in embodiments is directed to in situ processes for the preparation of hydroxygallium phthalocyanines wherein there can be avoided the use of a halo component, especially a chloro component such as chlorogallium phthalocyanine, as a precursor as it is known that such precursors can impart unfavorable properties to the aforementioned photoconductive members.

The Type V hydroxygallium phthalocyanine prepared by the processes of the present invention can be selected as photogenerator components in photoresponsive imaging members. These photoresponsive, or photoconductive imaging members may contain separate charge transport layers, especially hole transport layers containing hole transport molecules such as known tertiary aryl amines. The aforementioned photoresponsive imaging members can be negatively charged when the photogenerating layer is situated between the hole transport layer and the substrate, or positively charged when the hole transport layer is situated between the photogenerating layer and the supporting substrate. The layered photoconductor imaging members can be selected for a number of different known imaging and printing processes including, for example, electrophotographic imaging processes, especially xerographic imaging and other printing processes wherein negatively charged or positively charged images are rendered visible with toner compositions of the appropriate charge. The imaging members containing the hydroxygallium phthalocyanines are sensitive in the wavelength regions of from about 500 to about 900 nanometers, therefore, diode lasers can be selected as the light source, especially diode lasers which emit light in the region of from 700 to 850 nanometers.

In embodiments, the present invention is directed to a process for the preparation of the Type V polymorph of hydroxygallium phthalocyanine, which comprises the reaction of a gallium alkoxide with ortho-phthalodinitrile or 1,3-diiminoisoindoline, in a diol in the absence or in the presence of a solvent to obtain an alkoxy-bridged gallium phthalocyanine dimer, which dimer is hydrolyzed and converted to Type V hydroxygallium phthalocyanine. The aforementioned hydrolysis and conversion involves hydrolyzing the precursor dimer by dissolving it in a strong acid and then reprecipitating the resulting dissolved pigment in water, or an aqueous solvent, such as aqueous ammonia, thereby forming the Type I polymorph of hydroxygallium phthalocyanine; and treating the Type I hydroxygallium phthalocyanine formed with a polar aprotic organic solvent, for example N,N-dimethylformamide, N-methylpyrrolidinone, dimethylsulfoxide or pyridine to convert it to Type V hydroxygallium phthalocyanine.

The preparation of hydroxygallium phthalocyanine, and certain polymorphs of hydroxygallium phthalocyanine has been described in the literature.

In *Bull. Soc. Chim. Fr.*, 23 (1962), there is illustrated the preparation of hydroxygallium phthalocyanine via the precursor chlorogallium phthalocyanine. The precursor chlorogallium phthalocyanine is prepared by reaction of o-Cyanobenzamide with gallium chloride in the absence of solvent. o-Cyanobenzamide is heated to its melting point (172° C.), and to it is added gallium chloride, at which time the temperature is increased to 210° C. for 15 minutes, and then cooled. The solid is recrystallized out of boiling chloronaphthalene, to provide purple crystals having carbon, hydrogen and chlorine analyses matching theoretical values for chlorogallium phthalocyanine. Dissolution in concentrated sulfuric acid, followed by reprecipitation in diluted aqueous ammonia affords material having carbon, and hydrogen analyses matching theoretical values for hydroxygallium phthalocyanine.

In *Inorg. Chem.* (19), 3131, (1980), there is illustrated the preparation of chlorogallium phthalocyanine by reaction of o-phthalodinitrile with gallium chloride in the solvent quinoline.

Further, there are illustrated in JPLO 1-221459 (Toyo Ink Manufacturing) processes for preparing chlorogallium phthalocyanines and hydroxygallium phthalocyanines, and photoreceptors for use in electrophotography comprising a charge generation material and charge transport material on a conductive substrate, and wherein the charge generation material comprises one or a mixture of two specific gallium phthalocyanine compounds.

A number of hydroxygallium phthalocyanine polymorphs and processes for the preparation thereof are described in the JPLO 5-263007, the disclosure of which is totally incorporated herein by reference. One of the polymorphs, described herein as Type V hydroxygallium phthalocyanine is described in the JPLO 5-263007 by its X-ray diffraction pattern, which shows intense diffraction peaks at Bragg angles 7.5, 9.9, 12.5, 16.3, 18.6, 21.9, 23.9, 25.1 and 28.3, with the highest peak at 7.5 degrees 2Θ (2 theta±0.2°) in the X-ray diffraction spectrum.

The Type V hydroxygallium phthalocyanine is prepared, for example, from chlorogallium phthalocyanine obtained by the reaction of gallium chloride in a solvent, such as 1-chloronaphthalene, with orthophthalodinitrile or 1,3-diiminoisoindoline, hydrolyzing the pigment precursor chlorogallium phthalocyanine by standard methods, for example acid pasting, whereby the pigment precursor is dissolved in concentrated sulfuric acid and then reprecipitated in a solvent, such as water, or a dilute ammonia solution; and subsequently treating or contacting the resulting Type I hydroxygallium phthalocyanine with a solvent, such as N,N-dimethylformamide by, for example, ball milling in the presence of spherical glass beads to provide Type V hydroxygallium phthalocyanine.

Also, in U. S. Pat. No. 5,473,064, the disclosure of which is totally incorporated herein by reference, there is illustrated a process for the preparation of Type V hydroxygallium phthalocyanine, essentially free of chlorine, whereby a chlorogallium phthalocyanine pigment precursor is prepared by reaction of gallium chloride with 1,3-diiminoisoindoline in a solvent such as N-methylpyrrolidone; hydrolyzing said pigment precursor chlorogallium phthalocyanine by, for example, dissolving the pigment precursor in concentrated sulfuric acid, and then reprecipitating in a solvent, such as water, or a dilute ammonia solution; and subsequently treating the resulting hydroxygallium phthalocyanine with a solvent, such as N,N-dimethylformamide, by for example, ball milling said hydroxygallium phthalocyanine pigment in the presence of spherical glass beads. The Type V hydroxygallium phthalocyanine obtained from the chlorogallium phthalocyanine precursor prepared according to this procedure contains very low levels of residual chlorine of from about 0.001 percent to about 0.1 percent of the weight of the Type V hydroxygailium pigment as determined by elemental analysis and can enable improved electrical performance of the Type V hydroxygallium as a photogenerating pigment, and improved desirable dark decay and cycling characteristics for the resulting photoconductive imaging member.

Further in U.S. Pat. No. 5,407,766, the disclosure of which is totally incorporated herein by reference, there is illustrated a process for the preparation of Type V hydroxygallium phthalocyanine, which comprises formation of a nonchlorinated gallium phthalocyanine precursor prepared by reaction of 1,3-diiminoisoindoline with gallium acetylacetonate in a suitable solvent; hydrolyzing the precursor by dissolving in a strong acid and then reprecipitating the dissolved pigment in aqueous ammonia, thereby forming hydroxygallium phthalocyanine; and admixing the hydroxygallium phthalocyanine with a polar aprotic organic solvent, such as N,N-dimethylformamide, to obtain Type V hydroxygallium phthalocyanine that possesses improved electrical characteristics for the Type V hydroxygallium pigment and wherein there is enabled in embodiments Type V with lower pico/seconds, improved dark decay and improved cycling characteristics for the layered imaging member thereof.

In the aforementioned documents, synthesis and processing conditions were disclosed for the preparation of hydroxygallium phthalocyanines, including Type V hydroxygallium phthalocyanine which could be used in electrophotographic applications. Complex electrophotographic properties such as photosensitivity, dark decay, cyclic stability and environmental stability of photoconductive members, or electrophotographic photoreceptors are primarily dependent on=n purity, dopants, morphology, crystal defects and analytical differences in the pigments. These differences in the electrophotographical properties of a pigment, often a particular polymorph, are usually traced to the processes by which the pigment was obtained, or to the pigment precursor used to obtain a certain polymorph.

To obtain a phthalocyanine based electrophotographic photoreceptor having high sensitivity to near infrared light, it is believed necessary to control the purity and chemical structure of the pigment, as well as to prepare the pigment in the correct crystal modification, as is generally the situation with many organic photoconductors. It is also known that certain impurities, such as ionic species, or sulfur in some situations, as well as phthalocyanine ring chlorination, even at very low levels, can be detrimental. Thus, there is a need for processes in which the pigments are obtained in high purity, acceptable yields and with superior electrophotographic properties.

In the present application, there are disclosed processes for the preparation of Type V hydroxygallium phthalocyanine using as precursor an alkoxy-bridged gallium phthalocyanine, the formula and preparation thereof being described in the copending applications. This method is an improvement over the prior art in that, for example, it does not use chlorogallium phthalocyanine as a precursor. Undesirable ring chlorination which often occurs in the preparation of chlorogallium phthalocyanine as gallium chloride is used at high temperature in the synthesis, and such chlorination can be avoided or minimized with the processes of the present invention.

In comparison, in the synthesis of an alkoxy-bridged gallium phthalocyanine dimer, gallium chloride is converted to a less-reactive gallium alkoxide prior to the phthalocyanine synthesis being performed at elevated temperature.

The alkoxy-bridged gallium phthalocyanine dimer precursor can be hydrolyzed to hydroxygallium phthalocyanine by standard methods, such as by treatment with sulfuric acid, using a procedure similar to that described for the hydrolysis of chlorogallium phthalocyanine in *Bull. Soc. Chim. Fr.*, 23 (1962), and then converting the hydroxygallium phthalocyanine to the Type V hydroxygallium phthalocyanine polymorph, as described, for example, in JPLO 5-263007. By using an alkoxy-bridged gallium phthalocyanine dimer precursor for Type V hydroxygallium phthalocyanine, any negative effects of residual chlorine, or ring chlorination are avoided. The invention process is a high yield, high purity, and economical process for the preparation of Type V hydroxygallium phthalocyanine. Furthermore, the Type r hydroxygallium phthalocyanine obtained, according to this method, from an alkoxy-bridged gallium phthalocyanine dimer precursor, shows superior electrophotographic properties when compared to Type V hydroxygallium phthalocyanine obtained according to the prior art.

In the following patents and copending patent applications filed concurrently herewith there is illustrated: U.S. Pat. No. 5,466,796 alkoxy-bridged metallophthalocyanine dimers of the formula $C_{32}H_{16}N_8MOROMN_8H_{16}C_{32}$, or of the formula

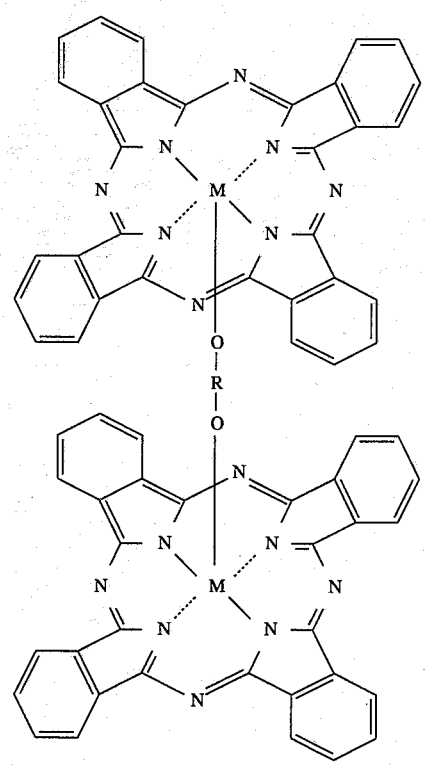

wherein M is a metal, and R is an alkyl or an alkyl ether; U.S. Pat. No. 5,456,998 a photoconductive imaging member comprised of an alkoxy-bridged metallophthalocyanine dimer as a charge generator material, wherein the dimer is of the formula $C_{32}H_{16}N_8MOROMN\ N_8H_{16}C_{32}$ wherein M is a trivalent metal, and R is an alkyl group or an alkyl ether group

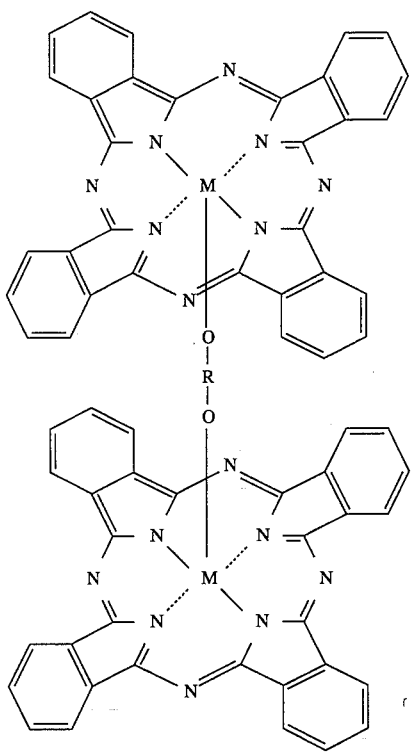

and U.S. Ser. No. 233,195 is a process for the preparation of alkoxy-bridged metallophthalocyanine dimers by the reaction of a trivalent metal compound with ortho-phthalodinitrile or 1,3-diiminoisoindoline in the presence of a diol.

The disclosures of all of the aforementioned publications, laid open applications, copending applications and patents are totally incorporated herein by reference.

SUMMARY OF THE INVENTION

It is an object of the present invention to provide processes for the preparation of hydroxygallium phthalocyanine and imaging members thereof with many of the advantages illustrated herein.

Another object of the present invention relates to the provision of improved layered photoresponsive imaging members with near infrared photosensitivity.

In a further object of the present invention there are provided in situ processes for the preparation of Type V hydroxygallium phthalocyanine with the X-ray diffraction pattern (XRD) with peaks at Bragg angles of 7.4, 9.8, 12.4, 12.9, 16.2, 18.4, 21.9, 23.9, 25.0 and 28.1, with the highest peak at 7.4 degrees 2Θ (2 theta±0.2°).

It is yet another object of the present invention to provide high yield, simple and economical processes for the preparation of Type V hydroxygallium phthalocyanine from an alkoxy-bridged gallium phthalocyanine dimer as precursor.

Another object of the present invention is to provide processes for the preparation of Type V hydroxygallium phthalocyanine from an alkoxy-bridged gallium phthalocyanine dimer, wherein the processes are economical primarily because they circumvent the high cost and the limited availability of gallium alkoxides.

A further object of the present invention relates to the preparation of electrically superior Type V hydroxygallium phthalocyanine in acceptable yield, exceeding 60 weight percent and, more specifically, from about 60 percent to about 90 percent, and wherein residual halogens, such as chlorine, are not contained in the product, which halogens adversely affect the photoconductive characteristics of imaging members with Type V hydroxygallium phthalocyanine as the photogenerating pigment.

In yet a further object of the present invention there are provided processes for the preparation of Type V hydroxygallium phthalocyanine that can be selected as a photogenerator pigment in layered photoconductive imaging members and which members, in embodiments, possess excellent cyclic stability and excellent dark decay characteristics.

In a further object of the present invention there are provided photoresponsive imaging members with a photogenerator layer comprised of Type V hydroxygallium phthalocyanine pigment components obtained by the processes illustrated herein.

In still a further object of the present invention there are provided photoresponsive imaging members with an aryl amine hole transport layer, and a photogenerator layer comprised of Type V hydroxygallium phthalocyanine pigment components obtained by the processes illustrated herein.

These and other objects of the present invention can be accomplished in embodiments thereof by the provision of processes for the preparation of hydroxygallium phthalocyanine, especially the Type V polymorph, and photoresponsive imaging members thereof. More specifically, in embodiments of the present invention there are provided processes for the preparation of Type V hydroxygallium phthalocyanine which comprise providing a precursor alkoxy-bridged gallium phthalocyanine dimer by, for example, the reaction of a gallium alkoxide with ortho-phthalodinitrile or 1,3-diiminoisoindoline and a diol, reference U.S. Pat. No. 5,466,796, the disclosure of which is totally incorporated herein by reference, and thereafter subjecting the dimeric phthalocyanine to hydrolysis to form hydroxygallium phthalocyanine, and subsequently converting to the desired Type V polymorph of hydroxygallium phthalocyanine. In embodiments, the present invention relates to an in situ process for the preparation of Type V hydroxygallium phthalocyanine which comprises the formation of an alkoxy-bridged gallium phthalocyanine dimer hydrolyzing said alkoxy-bridged gallium phthalocyanine dimer to hydroxygallium phthalocyanine, and subsequently converting the hydroxygallium phthalocyanine product obtained to Type V hydroxygallium phthalocyanine; and wherein the dimer is obtained by the reaction gallium trichloride with an alkali metal oxide in a solvent; thereafter removing the alkali metal halide byproduct; and reacting the obtained gallium alkoxide solution with ortho-phthalodinitrile or 1,3-diiminoisoindoline and a diol. The alkoxybridged gallium phthalocyanine dimer precursor for the preparation of hydroxygallium phthalocyanine can be of the general formula $C_{32}H_{16}N_8GaOROGaN_8H_{16}C_{32}$ as illustrated by Formula 1.

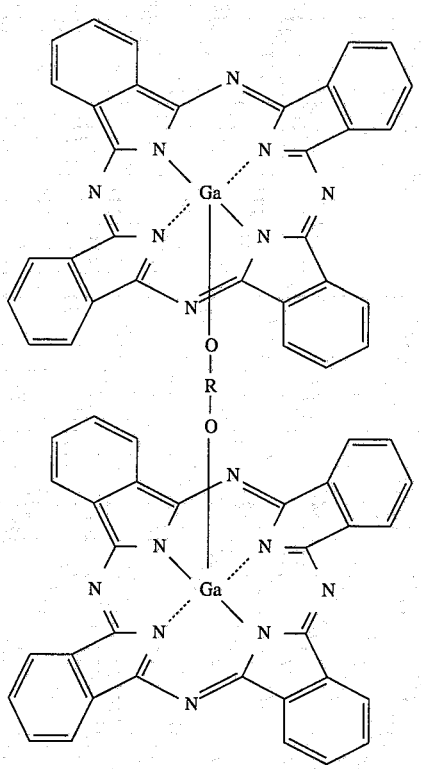

FORMULA 1 with, for example, from 2 to about 10, and preferably about 2 to 6 carbon atoms in the alkoxy-bridging unit (O—R—O) wherein R is an alkyl group or an alkyl ether, and wherein Ga can be another trivalent metal. Accomplishing the phthalocyanine syntheses in different diol solvents results in the formation of the different corresponding alkoxy-bridged gallium phthalocyanine dimers. For example, using 1,2-ethanediol (ethylene glycol) as reactant and as reaction solvent for the alkoxy-bridged gallium phthalocyanine dimer synthesis, there is provided the dimer which incorporates the ethanediol fragment into the structure and has the specific formula $C_{32}H_{16}N_8GaOCH_2CH_2OGaN_8H_{16}C_{32}$. Similarly, using, for example, 1,3-propanediol in the alkoxy-bridged gallium phthalocyanine dimer synthesis there is provided the dimer which incorporates the propanediol fragment into the structure and has the specific formula $C_{32}H_{16}N_8GaOCH_2CH_2CH_2OGaN_8H_{16}C_{32}$.

In embodiments, there are provided in situ processes by which the gallium alkoxide required for the alkoxy-bridged gallium phthalocyanine dimer synthesis is prepared prior to the phthalocyanine synthesis, and the gallium alkoxide solution is treated in order to remove the salt byproduct, prior to the phthalocyanine synthesis. The gallium alkoxide can be synthesized from gallium chloride and an alkali metal alkoxide, which results in an insoluble alkali metal chloride salt byproduct being formed. Removal of the salt byproduct prior to the phthalocyanine synthesis requires a separation step, for example filtration.

There are provided processes by which the gallium alkoxide required for the alkoxy-bridged gallium phthalocyanine dimer synthesis is prepared as an integral part of the phthalocyanine synthesis. The gallium alkoxide is synthesized from gallium chloride and an alkali metal alkoxide, which results in an insoluble alkali metal chloride salt byproduct being formed. The other reactants, such as o-phthalodinitrile and a diol are added to the gallium alkoxide mixture containing the salt byproduct, and the phthalocyanine synthesis is performed in a one-pot synthesis, referred to as an "in situ" synthesis.

The process of the present invention comprises the preparation of an alkoxy-bridged gallium phthalocyanine dimer, and the subsequent hydrolysis of the resulting phthalocyanine dimer to hydroxygallium phthalocyanine by dissolving the dimer in a concentrated acid like sulfuric acid, and then adding the phthalocyanine solution to an aqueous solution to precipitate hydroxygallium phthalocyanine Type I. The hydroxygallium phthalocyanine obtained by hydrolysis of the dimer is then converted to Type V hydroxygallium phthalocyanine by treatment or contacting with a polar aprotic organic solvent, for example N,N-dimethylformamide. In embodiments of the present invention, a hydroxygallium phthalocyanine with an X-ray diffraction pattern having major peaks at Bragg angles of 6.8, 13.0, 16.5, 21.0, 26.3 and 29.5, with the highest peak at 6.8 degrees 2Θ (2 theta ±0.2°), described as Type I hydroxygallium phthalocyanine is obtained by hydrolysis of an alkoxy-bridged gallium phthalocyanine dimer, and it is then converted to a hydroxygallium phthalocyanine with an X-ray diffraction pattern having major peaks at Bragg angles of 7.4, 9.8, 12.4, 12.9, 16.2, 18.4, 21.9, 23.9, 25.0 and 28.1, with the highest peak at 7.4 degrees 2Θ (2 theta ±0.2°), referred to as Type V hydroxygallium phthalocyanine. In preferred embodiment, the alkoxy-bridged gallium phthalocyanine dimer is 1,2-di(oxogallium phthalocyaninyl) ethane, characterized by elemental analysis (including absence of chlorine), infrared spectroscopy, $^1H$ NMR spectroscopy, $^{13}C$ solid state CP/MAS NMR spectroscopy and X-ray powder diffraction. Infrared spectroscopy of 1,2-di(oxogallium phthalocyaninyl) ethane was performed by diffuse reflectance: major peaks at 573, 611,636, 731,756, 775, 874, 897,962,999, 1069, 1088, 1125, 1165, 1289, 1337, 1424, 1466, 1503, 1611, 2569, 2607, 2648, 2864, 2950, and 3045 cm$^{-1}$ (FIG. 1). Infrared of the dimer does not show the characteristic broad hydroxyl group peak of hydroxygallium phthalocyanine at about 3490 cm$^{-1}$ (see FIGS. 4 and 6), or the hydroxyl group peak expected for ethanediol (3300 to 3400 cm$^{-1}$). $^1H$ NMR spectroscopy (in trifluoroacetic acid, TFA-d/CDCl$_3$ solution, 1:1 v/v, tetramethylsilane reference) has peaks at (δ, ppm±0.01 ppm) 4.00 (4H), 8.54 (16H), and 9.62 (16H). The relative integration of 4 protons being the two CH$_2$ units from the alkoxy-bridging unit (—OCH$_2$CH$_2$O—) between the two gallium phthalocyanine moieties, and the phthalocyanine dimer ring hydrogens appear as two sets of 16 protons. The incorporated ethanediol (which forms the bridge) is liberated by hydrolysis during dissolution of the dimer in the TFA-d/CDCl$_3$ solvent (FIG. 2). The $^{13}C$ solid state CP/MAS (cross polarization/magic angle spinning) NMR spectrum has peaks at (δ, ppm±1 ppm) 60.8 (2CH$_2$), 124.0 (16CH), 129.1 (16CH), 135.5 (16C), 152.6 (16C). All the NMR data are consistent with the formula $C_{32}H_{16}N_8GaOCH_2CH_2OGaN_8H_{16}C_{32}$ for 1,2-di(oxogallium phthalocyaninyl) ethane. The X-ray diffraction pattern has major peaks at Bragg angles of (2 Θ±0.2°)6.7, 8.9, 12.8, 13.9, 15.7, 16.6, 21.2, 25.3, 25.9 and 28.3, with the highest peak at 6.7 degrees 2Θ (FIG. 3).

Embodiments of the present invention are directed to processes for the preparation of Type V hydroxygallium phthalocyanine, which comprise the dissolution of 1 part gallium chloride in about 1 part to about 100 parts, and preferably about 10 parts, of an organic solvent, such as benzene, toluene, xylene or the like, at a temperature of from about 0 to 100° C., and preferably at a temperature of about 25° C., to form a solution of gallium chloride; followed by the addition of 3 parts of an alkali metal alkoxide, such as sodium methoxide, sodium ethoxide, sodium propoxide or the like, preferably in a solution form, to produce a gallium alkoxide solution, and an alkali metal salt byproduct, for example sodium chloride, at a temperature of from about 0 to about 100° C., and preferably at a temperature of about 20 to about 40° C., followed by the reaction with from about 1 part to about 10 parts, and preferably about 4 parts, ortho-phthalodinitrile or 1,3-diiminoisoindolene, and a diol, such as 1,2-ethanediol (ethylene glycol), 1,2-propanediol (propylene glycol) or 1,3-propanediol, in an amount of from about 3 parts to about 100 parts, and preferably about 10 parts for each part of gallium alkoxide formed at a temperature of from about 150 to about 220° C., and preferably at a temperature of 195° C. for a period of 30 minutes to 6 hours, and preferably about 2 hours to provide an alkoxy-bridged gallium phthalocyanine dimer pigment precursor; which product photogenerating pigment is isolated by filtration at a temperature of about 20° C. to about 180° C., and preferably at about 120° C. to provide a dark blue solid. The isolated pigment is subsequently washed with an organic solvent Such as dimethylformamide at a temperature of from about 20° C. to about 120° C., and preferably at a temperature of about 80° C., followed by washing with aqueous solvents, such as aqueous ammonium hydroxide, aqueous sodium hydroxide, or the like, cold or hot water, and possibly another organic solvent wash to provide a pure form of the alkoxy-bridged gallium phthalocyanine dimer. Each different diol used for the phthalocyanine synthesis will produce a particular alkoxy-bridged gallium phthalocyanine dimer product, as determined by, for example, infrared (IR) spectroscopy, nuclear magnetic resonance (NMR) and X-ray powder diffraction pattern (XRD). The alkoxy-bridged gallium phthalocyanine dimer pigment (1 weight part) is dissolved in concentrated sulfuric acid (about 95 percent) in an amount of from about 1 weight part to about 100 weight parts, and in an embodiment about 25 weight parts, by stirring said pigment in the acid for an effective period of time, from about one minute to about 24 hours, and in an embodiment about 2 hours, at a temperature of from about 0° C. to about 75° C., and preferably about 40° C. in air or under an inert atmosphere such as argon or nitrogen; adding the resulting mixture at a controlled rate to a stirred solvent, such as water or a basic aqueous solution, which can be an aqueous ammonia solution of from about 3 molar to about 15 molar concentration, and preferably about 6 molar to 10 molar concentration, selecting from about 1 volume part to about 10 volume parts of the basic solution for each volume part of sulfuric acid that was used such that at the end of the precipitation step the pH of the pigment suspension should be over 7, which solvent is chilled while being stirred, in order to maintain a temperature from about −5° C. to about 40° C. during the pigment precipitation; isolating the resulting blue pigment by, for example, filtration, and washing the hydroxygallium phthalocyanine product obtained with deionized water by, for example, repeatedly redispersing and filtering the pigment until the filtrate is of neutral pH. The product is a dark blue solid with an X-ray diffraction pattern having major peaks at Bragg angles of 6.8, 13.0, 16.5, 21.0, 26.3 and 29.5, with the highest peak at 6.8 degrees 2Θ (2 theta ±0.2°), described as Type I hydroxygallium phthalocyanine. The Type I hydroxygallium phthalocyanine product obtained can be contacted or treated with a polar aprotic solvent, such as N,N-dimethylformamide, N-methylpyrrolidone, or the like by, for example, stirring, ball milling or otherwise contacting said Type I hydroxygallium phthalocyanine pigment with the aforementioned solvent in the absence or presence of grinding media such as stainless steel shot, spherical or cylindrical ceramic media, or spherical glass beads, at a temperature from about 0° C. to about 40° C. for a period of from about 2 hours to about 1 week, and preferably about 12 to 24 hours, such that there is obtained a Type V hydroxygallium phthalocyanine polymorph with an X-ray diffraction pattern having major peaks at Bragg angles of 7.4, 9.8, 12.4, 12.9, 16.2, 18.4, 21.9, 23.9, 25.0 and 28.1, with the highest peak at 7.4 degrees 2Θ (2 theta ±0.2°).

Preferred embodiments of the present invention are directed to in situ processes for the preparation of Type V hydroxygallium phthalocyanine, which comprise the dissolution of 1 part gallium chloride in about 1 part to about 100 parts, and preferably 10 parts of toluene at a temperature of from about 0° C. to about 100° C., and preferably at a temperature of about 25° C, to form a solution of gallium chloride; followed by the addition of 3 parts of a sodium methoxide solution in methanol to form a gallium methoxide solution and sodium chloride byproduct, for example, at a temperature of from about 0° C. to about 100° C., and preferably at a temperature of about 20° C. to about 40° C., followed by reaction with from about 1 part to about 10 parts, and preferably about 4 parts of ortho-phthalodinitrile, and 1,2-ethanediol (ethylene glycol) in an amount of from about 3 parts to about 100 parts, and preferably about 10 parts for each part of gallium alkoxide formed at a temperature of from about 150° to about 220° C., and preferably at a reflux temperature of about 190° C. to about 195° C. for a period of 20 minutes to 6 hours, and preferably about 2 hours to provide an alkoxy-bridged gallium phthalocyanine dimer pigment precursor; which dimer pigment is isolated by filtration at a temperature of about 20° C. to about 180° C., and preferably at about 120° C. to give a dark blue solid. The isolated pigment is subsequently washed with an organic solvent such as dimethylformamide at a temperature of from about 20° C. to about 120° C., and preferably at a temperature of about 80° C., followed by washing with hot water, and another organic solvent wash to provide a pure form of the precursor alkoxy-bridged gallium phthalocyanine dimer in a yield of about 75 percent, calculated based upon the amount of gallium chloride used. The specific alkoxy-bridged gallium phthalocyanine dimer product resulting from the synthesis using ethylene glycol is 1,2-di(oxogallium phthalocyaninyl) ethane, $C_{32}H_{16}N_8GaOCH_2CH_2OGaN_8H_{16}C_{32}$, having an XRD pattern with major peaks at Bragg angles of 6.7, 8.9, 12.8, 13.9, 15.7, 6.6, 21.2, 25.3, 25.9 and 28.3, with the highest peak at 6.7 degrees 2Θ (2 theta±0.2° ). The 1,2-di(oxogallium phthalocyaninyl) ethane pigment precursor (1 weight part) is dissolved in concentrated sulfuric acid (95 to 98 percent) in an amount of from about 1 weight part to about 100 weight parts, and preferably about 25 to 30 weight parts by stirring the pigment in the acid for an effective period of time, from about 30 minutes to about 6 hours, and in an embodiment about 2 hours at a temperature of from about 0° C. to about 75° C., and preferably about 30° C. to 50° C. in air or under an inert atmosphere such as argon or nitrogen; adding the resulting mixture at a controlled rate to a stirred solvent, such as water, or a basic aqueous solution, such as aqueous ammonia solution of about 6 molar to 10 molar concentration, preferably with the aqueous ammonia solution in such an amount that at the end of the precipitation step the pH of the pigment suspension should be about 8 with the solvent being chilled and stirred in order to maintain a temperature of from about −5° C. to about 40° C. during the pigment precipitation, and preferably under 25° C.; isolating the resulting blue pigment by, for example, filtration; and washing the hydroxygallium phthalocyanine product obtained with deionized water by, for example, redispersing and filtering using portions of aleionized water, which portions are from about 10 volume parts to about 400 volume parts for each weight part of alkoxy-bridged gallium phthalocyanine dimer pigment precursor which was used. The product is a dark blue solid with an X-ray diffraction pattern having major peaks at Bragg angles of 6.8, 13.0, 16.5, 21.0, 26.3 and 29.5, with the highest peak at 6.8 degrees 2Θ (2 theta ±0.2°), described as Type I hydroxygallium phthalocyanine. The Type I hydroxygallium phthalocyanine product obtained can then be treated with a polar aprotic solvent, such as N,N-dimethylformamide, N-methylpyrrolidone, or the like, by, for example, ball milling the Type I hydroxygallium phthalocyanine pigment in the presence of spherical glass beads, approximately 1 millimeters to 6 millimeters in diameter, at about 25° C., for a period of from about 1 hour to about 1 week, and preferably about 1 to 24 hours, such that there is obtained a Type V hydroxygallium phthalocyanine with an X-ray diffraction pattern having major peaks at Bragg angles of 7.4, 9.8, 12.4, 12.9, 16.2, 18.4, 21.9, 23.9, 25.0 and 28.1, with the highest peak at 7.4 degrees 2Θ (2 theta ±0.2°).

In embodiments, the diol selected for the process of the present invention is as indicated herein and includes ethylene glycol. 1,3-propanediol, 2-methyl-1,3-propanediol, 2,2-dimethyl-1,3-propanediol, 1,3-butanediol, 2,3-butanediol. 1,4-butanediol, 1,4-cyclohexanediol or 1,6-hexanediol.

Moreover, in embodiments of the present invention there is provided a process for the preparation of Type V hydroxygallium phthalocyanine which comprises the in situ formation of an alkoxy-bridged gallium phthalocyanine dimer, hydrolyzing said alkoxy-bridged gallium phthalocyanine dimer to hydroxygallium phthalocyanine, and subsequently converting the hydroxygallium phthalocyanine product obtained to Type V hydroxygallium phthalocyanine.

The processes described in the present invention provide in embodiments a high yield, for example from 75 to 82 percent, of the precursor alkoxy-bridged gallium phthalocyanine dimer, and, therefore, a high yield for the final product Type V hydroxygallium phthalocyanine using raw materials readily available and process conditions amenable for large scale operations, such as at the 100 gallon scale. Furthermore, by converting the gallium chloride to a gallium alkoxide, the processes provided herein yield alkoxy-bridged gallium phthalocyanine dimers which do not contain detrimental impurities, such as organic chlorinated derivatives which can be observed when gallium chloride is used directly as the source of gallium in the synthesis of gallium phthalocyanines. The Type V hydroxygallium phthalocyanine obtained according to the present invention using an alkoxy-bridged gallium phthalocyanine dimer as precursor shows superior properties in photoresponsive imaging members when used as photogenerator material, in particular, lower dark decay and better cyclic stability compared to Type V hydroxygallium phthalocyanine obtained from other gallium phthalocyanine precursors, such as for example chlorogallium phthalocyanine.

In embodiments, the present invention relates to a process for the preparation of Type V hydroxygallium phthalocyanine which comprises the formation of an alkoxy-bridged gallium phthalocyanine dimer by the reaction of an organic gallium complex of, for example, a metal alkoxide like gallium alkoxide and corresponding halide precipitate, metal acetates like gallium acetate instead of the alkoxide, and the like with orthophthalodinitrile or 1,3-diiminoisoindoline and a diol; hydrolyzing the resulting alkoxy-bridged gallium phthalocyanine dimer to hydroxygallium phthalocyanine, and subsequently converting the hydroxygallium phthalocyanine product obtained to Type V hydroxygallium phthalocyanine; and a process for the preparation of Type V hydroxygallium phthalocyanine which comprises the formation of an alkoxy-bridged gallium phthalocyanine dimer by the reaction of a gallium alkoxide, which has been formed from reacting gallium trichloride in a solvent, with a sodium alkoxide, and selecting the resulting mixture of gallium alkoxide and sodium chloride byproduct for the reaction with ortho-phthalodinitrile or 1,3-diiminoisoindoline and a diol; hydrolyzing the resulting alkoxy-bridged gallium phthalocyanine dimer to hydroxygallium phthalocyanine; and subsequently converting the product obtained to Type V hydroxygallium phthalocyanine by a solvent treatment.

Numerous different photoresponsive imaging members with the Type V hydroxygallium phthalocyanine pigment obtained by the processes of the present invention can be fabricated. In embodiments, the layered photoresponsive imaging members are comprised of a supporting substrate, a charge transport layer, especially an aryl amine hole transport layer, and situated therebetween a photogenerator layer comprised of the Type V hydroxygallium phthalocyanine photogenerating pigment. Another embodiment of the present invention is directed to positively charged layered photoresponsive imaging members comprised of a supporting substrate, a charge transport layer, especially an aryl amine hole transport layer, and as a top overcoating layer Type r hydroxygallium phthalocyanine pigment obtained with the processes of the present invention. Moreover, there is provided in accordance with the present invention an improved negatively charged photoresponsive imaging member comprised of a supporting substrate, a thin adhesive layer, a photogenerating layer containing Type r hydroxygallium phthalocyanine photogenerator obtained by the processes of the present invention dispersed in a polymeric resinous binder, such as a poly(vinyl butyral), a polycarbonate, or a styrene-vinylpyridine block copolymer, and as a top layer, aryl amine hole transporting molecules dispersed in a polymeric resinous binder such as polycarbonate.

The photoresponsive imaging members of the present invention can be prepared by a number of known methods, the type of coating process, the coating process parameters and the order of coating of the layers being dependent on the member desired. The photogenerating and charge transport layers of the imaging members can be coated as solutions or dispersions onto selective substrates by the use of a spray coater, dip coater, extrusion coater, roller coater, wire-bar coater, slot coater, doctor blade coater, gravure coater, and the like, and dried at from 40° C. to about 200° C. for from 10 minutes to about 10 hours under stationary conditions or in an air flow. The coating is accomplished to provide a final coating thickness of from 0.01 to about 30 microns after it has dried. The fabrication conditions for a given layer can be tailored to achieve optimum performance and cost in the final device.

Imaging members of the present invention are useful in various electrostatographic imaging and printing systems, particularly those conventionally known as xerographic processes. Specifically, the imaging members of the present invention are useful in xerographic imaging processes wherein the Type V hydroxygallium phthalocyanine pigment absorbs light of a wavelength of from about 500 to about 900 nanometers, and preferably from about 700 to about 850 nanometers. In these known processes, electrostatic latent images are initially formed on the imaging member followed by development, and thereafter transferring the image to a suitable substrate.

Substrate layers of an effective thickness of, for example, from about 50 to about 1,000 microns selected for the imaging members of the present invention can be opaque or substantially transparent, and may comprise any suitable material having the requisite mechanical properties. Thus, the substrate may comprise a layer of insulating material including inorganic or organic polymeric materials, such as MYLAR® a commercially available polyester, MYLAR® containing titanium, a layer of an organic or inorganic material having a semiconductive surface layer, such as indium tin oxide, or aluminum arranged thereon, or a conductive material inclusive of aluminum, chromium, nickel, brass or the like. The substrate may be flexible, seamless, or rigid and many have a number of many different configurations, such as for example a plate, a cylindrical drum, a scroll, an endless flexible belt and the like. In one embodiment, the substrate is in the form of a seamless flexible belt. In some situations, it may be desirable to coat on the back of the substrate, particularly when the substrate is a flexible organic polymeric material, an anticurl layer, such as for example polycarbonate materials commercially available such as MAKROLON®.

The photoconductive imaging member may optionally contain a charge blocking layer situated between the conductive substrate and the photogenerating layer. This layer may comprise metal oxides, such as aluminum oxide and the like, or materials such as silanes, or polymers such as polyesters. The primary purpose of this layer is to prevent charge injection from the substrate during and after charging.

Intermediate adhesive layers between the substrate and subsequently applied layers may be desirable to improve adhesion. Typical adhesive layers include film forming polymers such as polyester, polyvinylbutyral, polyvinylpyrrolidone, polycarbonate, polyurethane, polymethyl methacrylate, and the like, and mixtures thereof. Since the surface of the substrate can be a metal oxide layer or an adhesive layer, the expression "substrate" as employed herein is intended to include in embodiments a metal oxide layer with or without an adhesive layer on a metal oxide layer.

In addition, the photoconductive imaging member may also optionally contain an adhesive interface layer situated between the hole blocking layer and the photogenerating layer. This layer may comprise a polymeric material such as polyester, polyvinyl butyral, polyvinyl pyrrolidone, and the like.

With further regard to the imaging members, the photogenerator layer is preferably comprised of Type V hydroxygallium phthalocyanine obtained with the processes of the present invention dispersed in polymer binders. Generally, the thickness of the photogenerator layer depends on a number of factors, including the thicknesses of the other layers and the amount of photogenerator material contained in this layer. Accordingly, this layer can be of a thickness of from about 0.05 micron to about 10 microns when the hydroxygallium phthalocyanine photogenerator composition is present in an amount of from about 5 percent to about 100 percent by volume. In one embodiment, this layer is of a thickness of from about 0.25 micron to about 1 micron when the photogenerator composition is present in this layer in an amount of 30 to 75 percent by volume. The maximum thickness of this layer in an embodiment is dependent primarily upon factors, such as photosensitivity, electrical properties and mechanical considerations. The photogenerator layer can be fabricated by coating a dispersion of Type V hydroxygallium phthalocyanine obtained with the processes of the present invention in a suitable solvent with or without an optional polymer binder material. The dispersion can be prepared by mixing and/or milling the Type V hydroxygallium phthalocyanine in equipment such as paint shakers, ball mills, sand mills and attritors. Common grinding media such as glass beads, steel balls or ceramic beads may be used in this equipment. The binder resin may be selected from a number of known polymers such as poly(vinyl butyral), poly(vinyl carbazole), polyesters, polycarbonates, poly(vinyl chloride), polyacrylates and methacrylates, copolymers of vinyl chloride and vinyl acetate, phenoxy resins, polyurethanes, poly(vinyl alcohol), polyacrylonitrile, polystyrene, and the like. In embodiments of the present invention, it is desirable to select a coating solvent that does not disturb or adversely affect the other previously coated layers of the device. Examples of solvents that can be selected for use as coating solvents for the photogenerator layer are ketones, alcohols, aromatic hydrocarbons, halogenated aliphatic or aromatic hydrocarbons, ethers, amines, amides, esters, and the like. Specific examples are cyclohexanone, acetone, methyl ethyl ketone, methanol, ethanol, butanol, amyl alcohol, toluene, xylene, chlorobenzene, carbon tetrachloride, chloroform, methylene chloride, trichloroethylene, tetrahydrofuran, dioxane, dimethylformamide, dimethylacetamide, butyl acetate, ethyl acetate and methoxyethyl acetate, and the like.

The coating of the photogenerator layer in embodiments of the present invention can be accomplished with spray, dip or wire-bar methods such that the final dry thickness of the photogenerator layer is from 0.01 to 30 microns and preferably from 0.1 to 15 microns after being dried at 40° C. to 150° C. for 5 to 90 minutes.

Illustrative examples of polymeric binder materials that can be selected for the photogenerator pigment include those polymers as illustrated herein, and disclosed in U.S. Pat. No. 3,121,006, the disclosure of which is totally incorporated herein by reference. The binder resin may be selected from a wide number of polymers such as polyesters, poly(vinyl butyral), poly(vinyl carbazole), polycarbonates, poly(vinyl chloride), polyacrylates and methacrylates, phenoxy resins, polyurethanes, poly(vinyl alcohol), polyacrylonitrile, polystyrene, copolymers and block copolymers of selected monomers such as styrene and vinylpyridine, and the like. The solvents used to dissolve these binders depend upon the particular resin.

The charge transport layer is generally a nonphotoconductive material which supports the injection of photogenerated holes from the generator layer. The hole transporting layer is generally of a thickness of from about 5 microns to about 75 microns, and preferably of a thickness of from about 10 microns to about 40 microns. The charge transport layer may be a material comprising a hole transporting small molecule such as an aryl amine in an inactive, highly insulating and transparent polymer binder, or a charge transporting polymer such as an aryl amine polycondensation polymer. Aryl amines selected for the hole transporting layer include molecules of the following formula

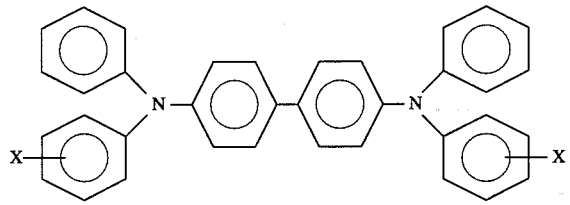

wherein X is an alkyl group or a halogen, especially those substituents selected from the group consisting of Cl and $CH_3$.

Examples of specific aryl amines are N,N'-diphenyl-N, N'-bis(alkylphenyl)- 1,1-biphenyl-4,4'-diamine wherein alkyl is selected from the group consisting of methyl, ethyl, propyl, butyl, hexyl, and the like; and N,N'-diphenyl-N,N'-bis(halophenyl)-1,1'-biphenyl-4,4'-diamine wherein the halo substituent is preferably a chloro substituent. Other known charge transport layer molecules can be selected, reference for example U.S. Pat. Nos. 4,921,773 and 4,464,450, the disclosures of which are totally incorporated herein by reference.

Charge transporting polymers, such as aryl amine polycondensation polymers, are described in U.S. Pat. Nos. 4,806,443 and 5,028,687, the disclosures of which are totally incorporated herein by reference, can also be selected.

Examples of the highly insulating and transparent polymer binder material for the transport layers include materials such as those described in U.S. Pat. No. 3,121,006, the disclosure of which is totally incorporated herein by reference. Specific examples of polymer binder materials include polycarbonates, acrylate polymers, vinyl polymers, cellulose polymers, polyesters, polysiloxanes, polyamides, polyurethanes and epoxies, as well as block, random or alternating copolymers thereof. Preferred electrically inactive binders are comprised of polycarbonate resins having a molecular weight of from about 20,000 to about 100,000 with a molecular weight of from about 50,000 to about 100,000 being particularly preferred. Generally, the transport layer contains from about 10 to about 75 percent by weight of the charge transport material, and preferably from about 35 percent to about 50 percent of this material.

Further details with regard to the layered photoconductive imaging member are illustrated in U.S. Pat. No. 5,456,998, the disclosure of which is totally incorporated herein by reference.

Also, included within the scope of the present invention are methods of imaging and printing with the photoresponsive devices illustrated herein. These methods generally involve the formation of an electrostatic latent image on the imaging member, followed by developing the image with a toner composition, reference U.S. Pat. Nos. 4,560,635; 4,298,697 and 4,338,390, the disclosures of which are totally incorporated herein by reference, subsequently transferring the image to a suitable substrate, and permanently affixing the image thereto. In those environments wherein the device is to be used in a printing mode, the imaging method involves the same steps with the exception that the exposure step can be accomplished with a laser device or image bar.

The xerographic electrical properties of the imaging members can be determined by known means, including as indicated herein electrostatically charging the surfaces thereof with a corona discharge source until the surface potentials, as measured by a capacitively coupled probe attached to an electrometer, attains an initial value $V_O$ of about −800 volts. After resting for 0.5 second in the dark, the charged members attain a surface potential of $V_{ddp}$, dark development potential. Each imaging member is then exposed to light from a filtered Xenon lamp with a XBO 150 watt bulb, thereby inducing a photodischarge which results in a reduction of surface potential to a $V_{bg}$ value, background potential. The desired wavelength and energy of the exposed light can be determined by the type of filters placed in front of the lamp. The monochromatic light photosensitivity is determined by using a narrow band-pass filter. The dark decay in volts per second was calculated as $(V_O-V_{ddp})/0.5$. The photosensitivity of the imaging members is provided in terms of the amount of exposure energy in ergs/cm², designated as $E_{1/2}$, required to achieve 50 percent photodischarge from the dark development potential. $E_{800-100V}$, which is the amount of exposure energy causing reduction of the $V_{ddp}$ from 800 volts to 100 volts, was also determined. The higher the photosensitivity is indicated by the smaller the $E_{1/2}$ and $E_{800-100V}$ values. Cyclic stability is determined by performing cycling tests. Devices were charged with a corotron to about −800 volts. They were exposed with 775 nanometers light with an intensity of about 7 ergs/cm² and erased with white light of about 60 ergs/cm². The dark development ($V_{ddp}$) and background ($V_{bg}$) potentials were measured and recorded while the testing was performed for 10,000 cycles. After the cycling test had been completed, the devices remained in the dark for about 20 hours. After charging the device to about −800 volts with a corotron, they were exposed with 775 nanometers light with an intensity of 3 ergs/cm² and erased with white light of about 200 ergs/cm². The dark development and background potentials were measured and recorded while the testing was performed for 5,000 cycles. The significantly higher erase light intensity, used in this second test compared to the standard test, accelerates the cycle-down (decrease in the dark development potential) in the photogenerator material and is thus considered a stress test. The smaller values of the voltage loss of both the dark development ($V_{ddp}$) and background ($V_{bg}$) potentials represent the better cyclic stability.

BRIEF DESCRIPTION OF THE DRAWINGS

For a better understanding of the present invention and further features thereof, reference is made to the following detailed description of various preferred embodiments wherein.

The following Examples are provided with Comparative Examples included. These Examples are intended to be illustrative only. The invention is not intended to be limited to the materials, conditions, or process parameters recited herein.

EXAMPLE I

Figure 1:
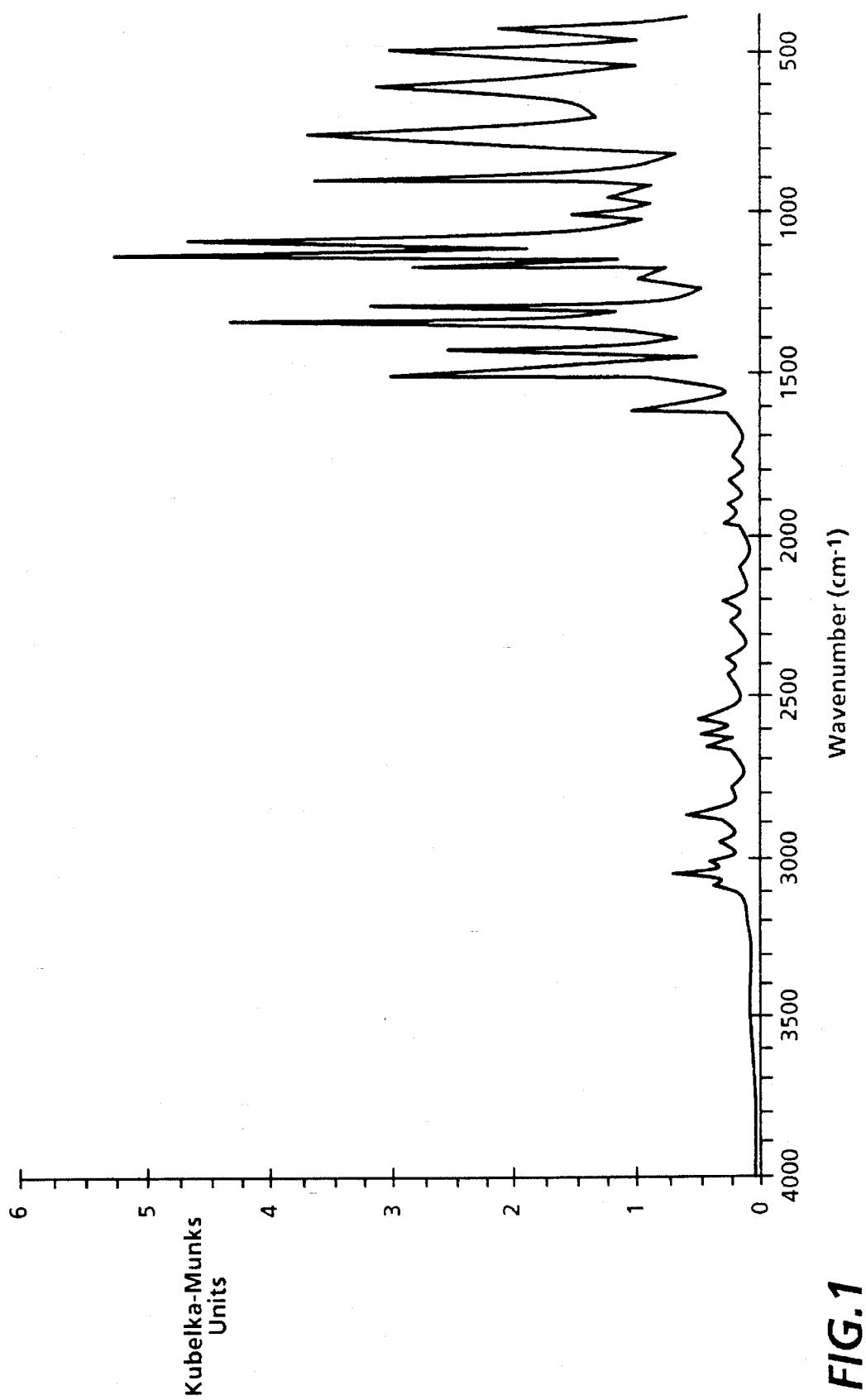
FIG. 1 represents an infrared plot of the alkoxy-bridged phthalocyanine dimer prepared as described in Example I, which has the formula $C_{32}H_{16}N_8GaOCH_2CH_2OGaN_8H_{16}C_{32}$.
Figure 2:
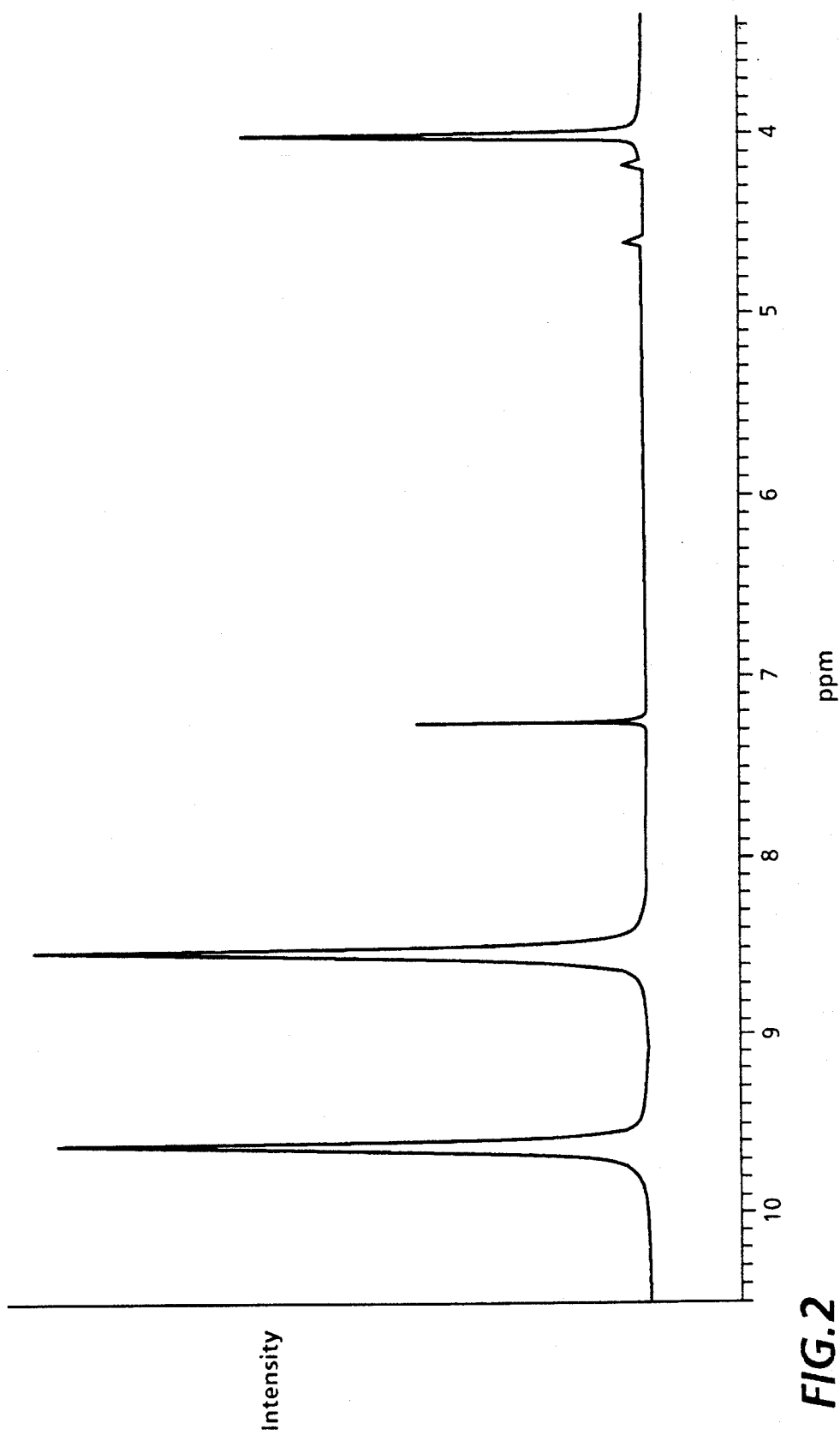
FIG. 2 represents a plot of ¹H NMR spectroscopy (in TFA-d/CDCl₃ solution) of the alkoxy-bridged phthalocyanine dimer prepared as described in Example I.
Figure 3:
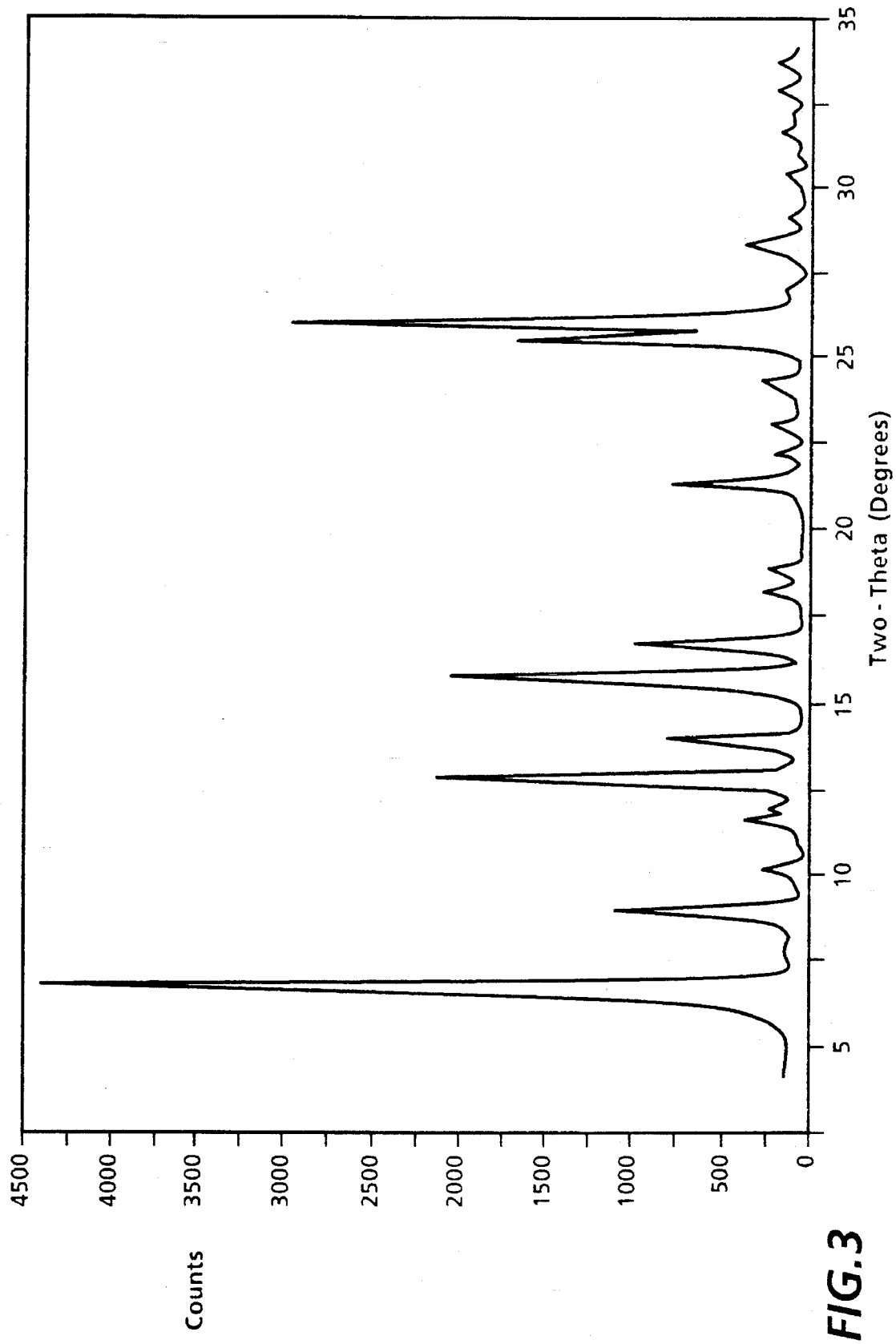
FIG. 3 represents an X-ray powder diffraction trace for the alkoxy-bridged gallium phthalocyanine dimer (Type I polymorph) prepared as described in Example I.

Alkoxy-bridged Gallium Phthalocanine Dimer Synthesis Using Gallium Methoxide Obtained From Gallium Chloride and Sodium Methoxide In Situ To a 1 liter round bottomed flask were added 25 grams of $GaCl_3$ and 300 milliliters of toluene and the mixture was stirred for 10 minutes to form a solution. Then, 98 milliliters of a 25 weight percent sodium methoxide solution (in methanol) was added while cooling the flask with an ice bath to keep the contents below 40° C. Subsequently, 250 milliliters of ethylene glycol and 72.8 grams of o-phthalodinitrile were added. The methanol and toluene were quickly distilled off over 30 minutes while heating from 70° C. to 135° C., and then the phthalocyanine synthesis was performed by heating at 195° C. for 2 hours. The alkoxy-bridged gallium phthalocyanine dimer was isolated by filtration at 120° C. The product was then washed with 400 milliliters of DMF at 100° C. for 1 hour and filtered. The product was then washed with 400 milliliters of deionized water at 80° C. for 1 hour and filtered. The product was then washed with 400 milliliters of methanol at 60° C. for 1 hour and filtered. The product was dried at 60° C. under vacuum for 18 hours. The alkoxy-bridged gallium phthalocyanine dimer, 1,2-di(oxogallium phthalocyaninyl) ethane, was isolated as a dark blue solid in 80 percent yield. The dimer product was characterized by elemental analysis, infrared spectroscopy, 1H NMR spectroscopy, 13C. solid state CP/MAS (cross polarization/magic angle spinning) NMR spectroscopy and X-ray powder diffraction. Elemental analysis showed the presence of 0.05 percent chlorine. Infrared spectroscopy major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 $cm^{-1}$ (FIG. 1); $^1H$ NMR spectroscopy (TFA-d/CDCl$_3$ solution, 1:1 v/v, tetramethylsilane reference) peaks at (δ, ppm ±0.01 ppm) 4.00 (4H), 8.54 (16H), and 9.62 (16H) (FIG. 2); $^{13}C$ solid state CP/MAS NMR spectroscopy peaks at (δ, ppm ±1 ppm) 60.2 (2CH$_2$), 124.2 (16CH), 129.1 (16CH), 135.1 (16C), 152.8 (16C); X-ray powder diffraction pattern peaks at Bragg angles (2Θ±0.2°) of 6.7, 8.9, 12.8, 13.9, 15.7, 16.6, 21.2, 25.3, 25.9, and 28.3, with the highest peak at 6.7 degrees 2Θ (FIG. 3).

EXAMPLE II

Large Scale Alkoxy-bridged Gallium Phthalocyanine Dimer Synthesis Using Gallium Methoxide Obtained From Gallium Chloride and Sodium Methoxide In Situ:

A 20 gallon glass-lined reactor was purged with nitrogen and charged with 32.0 kilograms of toluene. The reactor agitator was started and 3.00 kilograms of gallium trichloride were loaded through the reactor loading port. The reactor loading port was closed, a nitrogen purge started, and the agitator speed increased to 200 rpm, while cooling was applied to the reactor jacket by a recirculating cooling system, and 11.04 kilograms of sodium methoxide solution (25 weight percent in methanol) was charged to the reactor from an addition vessel over a period of 30 minutes. The reactor was then charged with 8.73 kilograms of o-phthalodinitrile and 20 kilograms of ethylene glycol. The reactor was purged with nitrogen after which heating was applied using hot oil supply to the reactor jacket. During heating to a reaction temperature of 195° to 200° C., methanol and toluene were removed by distillation. After 20 kilograms of distillate has been removed another 20 kilograms of ethylene glycol were charged in the reactor from an addition vessel over a period of 10 minutes. The reaction was accomplished for 5 hours at 195° to 200° C. At the end of the 5 hour reaction period, cooling was applied using the recirculating cooling system. When the reactor temperature was 90° C., the reactor contents were discharged into an agitated vacuum filter and the filtrate drained. The crude material was reslurry washed in the agitated vacuum filter two times with 50 kilograms of DMF used to rinse the reactor. The washing was accomplished two more times in the agitated vacuum filter with 100 kilograms of hot DMF at 75° C. to 90° C. The material was then reslurry washed three times in the agitated vacuum filter with 50 kilograms of deionized water at 75° C. to 90° C. The wet cake resulting was then reslurry washed in the agitated vacuum filter three additional times for 30 minutes with 50 kilograms of warm methanol (45° C.) and filtered. The material was dried at 60° C. in a vacuum shelf dryer. 8.51 Kilograms of alkoxy-bridged gallium phthalocyanine dimer of Example I were obtained as a dark blue solid (81.4 percent yield). The dimer product was characterized by elemental analysis, infrared spectroscopy, $^1H$ NMR spectroscopy, $^{13}C$ solid state CP/MAS (cross polarization/magic angle spinning) NMR spectroscopy and X-ray powder diffraction. Elemental analysis showed the presence of only 0.09 percent chlorine. Infrared spectroscopy major peaks at 573, 611, 636, 731, 756, 775, 874, 897, 962, 999, 1069, 1088, 1125, 1165, 1289, 1337, 1424, 1466, 1503, 1611, 2569, 2607, 2648, 2864, 2950, and 3045 $cm^1$ (identical to FIG. 1); $^1H$ NMR spectroscopy (TFA-d/CDCl$_3$ solution, 1:1 v/v, tetramethylsilane reference) peaks at (δ, ppm ±0.01 ppm) 4.00 (4H), 8.54 (16H), and 9.62 (16H) (identical to FIG. 2); $^{13}C$ solid state CP/MAS NMR spectroscopy peaks at (δ, ppm ±1 ppm) 60.5 (2CH$_2$), 123.4 (16CH), 128.5 (16CH), 135.0 (16C), 152.4 (16C); X-ray powder diffraction pattern peaks at Bragg angles (2Θ±0.2°) of 6.7, 8.9, 12.8, 13.9, 15.7, 16.6, 21.2, 25.3, 25.9, and 28.3, with the highest peak at 6.7 degrees 2Θ (identical to FIG. 3).

EXAMPLE III

Figure 4:
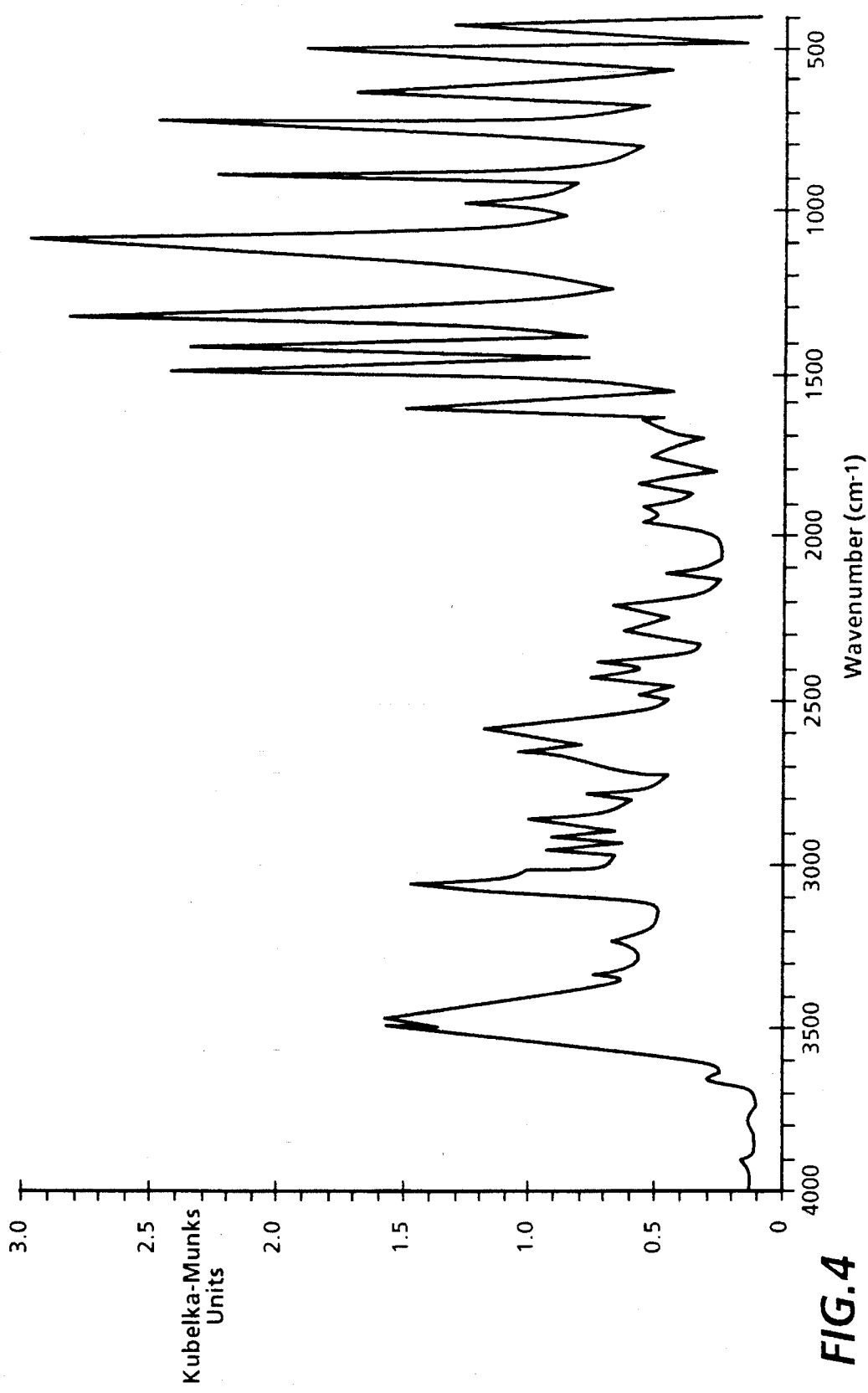
FIG. 4 represents an infrared plot of the Type 1hydroxygallium phthalocyanine prepared as described in Example III.
Figure 5:
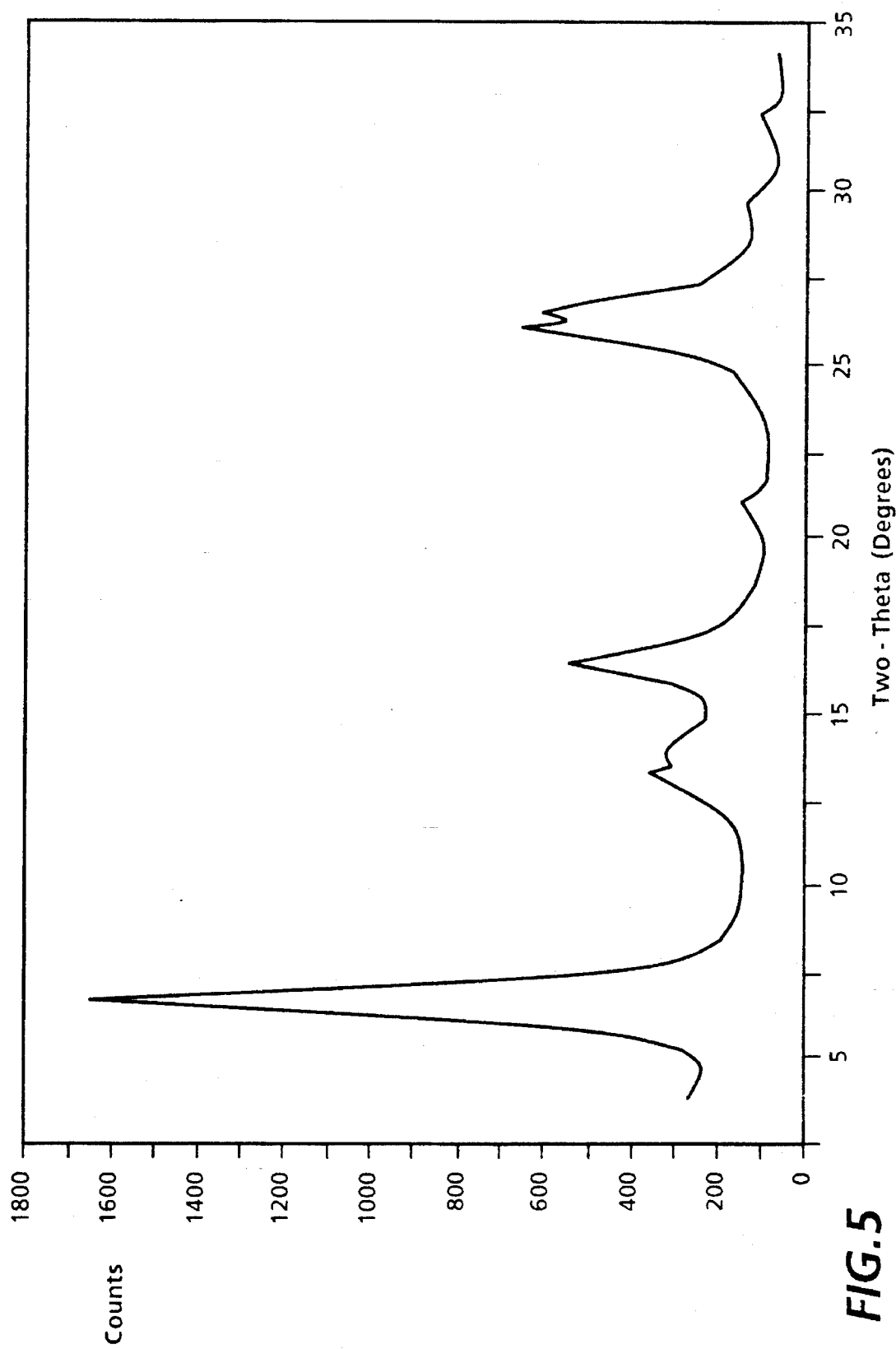
FIG. 5 represents an X-ray powder diffraction trace for the Type I hydroxygallium phthalocyanine prepared as described in Example III.

Hydrolysis of Alkoxy-bridged Gallium Phthalocyanine Dimer to Hydroxygallium Phthalocyanine The alkoxy-bridged gallium phthalocyanine dimer prepared as described in Example I was hydrolyzed as follows. Sulfuric acid (94 to 96 percent, 125 grams) was heated to 40° C. in a 125 milliliter Erlenmeyer flask and then 5 grams of the alkoxy-bridged gallium phthalocyanine dimer were added, while stirring, over approximately 15 minutes, during which time the temperature of the solution increased to about 48° C. The acid solution was then stirred for 2 hours at 40° C., after which it was added in a dropwise fashion to a mixture comprised of concentrated (~30 percent) ammonium hydroxide (265 milliliters) and aleionized water (435 milliliters), which had been cooled to a temperature below 5° C. Addition of the dissolved dimer pigment was completed in about 30 minutes, during which time the temperature of the solution increased to about 40° C. The reprecipitated pigment was then removed from the cooling bath and allowed to stir at room temperature for 1 hour. It was then filtered through a porcelain funnel fitted with a Whatman 934-AH grade glass fiber filter. The resulting blue pigment was redispersed in fresh aleionized water by stirring at room temperature for 1 hour and filtered as before. This process was repeated at least three times until the conductivity of the filtrate was <20 μS. The filtercake was oven dried overnight at 50° C. to provide 4.4 grams (88 percent) of Type I HOGaPc identified by infrared spectroscopy and X-ray powder diffraction. Infrared spectroscopy major peaks at 507, 573, 629, 729, 756, 772, 874, 898, 956, 984, 1092, 1121, 1165, 1188, 1290, 1339, 1424, 1468, 1503, 1588, 1611, 1757, 1835, 1951, 2099, 2207, 2280, 2384, 2425, 2570, 2608, 2652, 2780, 2819, 2853, 2907, 2951, 3049 and 3479 (very broad) cm$^{-1}$ (FIG. 4); X-ray diffraction pattern peaks at Bragg angles of 6.8, 13.0, 16.5, 21.0, 26.3 and 29.5, with the highest peak at 6.8 degrees 2Θ (2 theta ±0.2°) (FIG. 5).

EXAMPLE IV

Large Scale Hydrolysis of Alkoxy-bridged Gallium Phthalocyanine Dimer to Hydroxygallium Phthalocyanine The alkoxy-bridged gallium phthalocyanine dimer prepared as described in Example II above was hydrolyzed on a 3.0 kilogram scale in the following manner. Ninety kilograms of 96 percent reagent grade sulfuric acid was charged into a 30 gallon reactor and then the reactor agitator was set to run at 100 rpm. Next, 3.0 kilograms of the dimer was charged into the reactor over a period of 30 minutes, after which the reactor loading port was closed and the reactor was heated to 40° C. using a hot glycol heating system. The dimer dissolved in the acid while the agitation was continued at 40° C. for an additional 3.5 hours.

A 100 gallon reactor was charged with 200 kilograms of 26 percent aqueous ammonia solution and 75 kilograms of aleionized water, and then it was cooled to 0° C. using a cold glycol cooling system. The H$_2$SO$_4$ solution in the 30 gallon reactor was slowly added to the ammonia solution while agitating at 200 rpm, so that the temperature could be maintained below 10° C. by the cooling system. The addition consumed about 4 hours, during which time the phthalocyanine precipitated. The phthalocyanine slurry was then transferred to a 70 gallon plastic filter equipped with a polypropylene filter cloth, and the liquid was removed by vacuum filtration under continuous agitation. After most of the liquid had been removed, the phthalocyanine was repeatedly washed in the filter with portions of 150 kilograms of aleionized water, under continuous agitation and filtration, until the conductivity of the filtrate was under 20 micromhos. The wet cake was then transferred to a vacuum shelf dryer and dried at 80° to 85° C. under full vacuum for a minimum of 24 hours to provide 2.85 kilograms (95 percent yield) of Type I HOGaPc identified by infrared spectroscopy and X-ray powder diffraction. Infrared spectroscopy major peaks at 507, 573, 629, 729, 756, 772, 874, 898, 956, 984, 1092, 1121, 1165, 1188, 1290, 1339, 1424, 1468, 1503, 1588, 1611, 1757, 1835, 1951, 2099, 2207, 2280, 2384, 2425, 2570, 2608, 2652, 2780, 2819, 2853, 2907, 2951, 3049 and 3479 (very broad) cm$^{-1}$ (identical to FIG. 4); X-ray diffraction pattern peaks at Bragg angles of 6.8, 13.0, 16.5, 21.0, 26.3 and 29.5, with the highest peak at 6.8 degrees 2Θ (2 theta ±0.2°) (identical to FIG. 5).

EXAMPLE V

Figure 6:
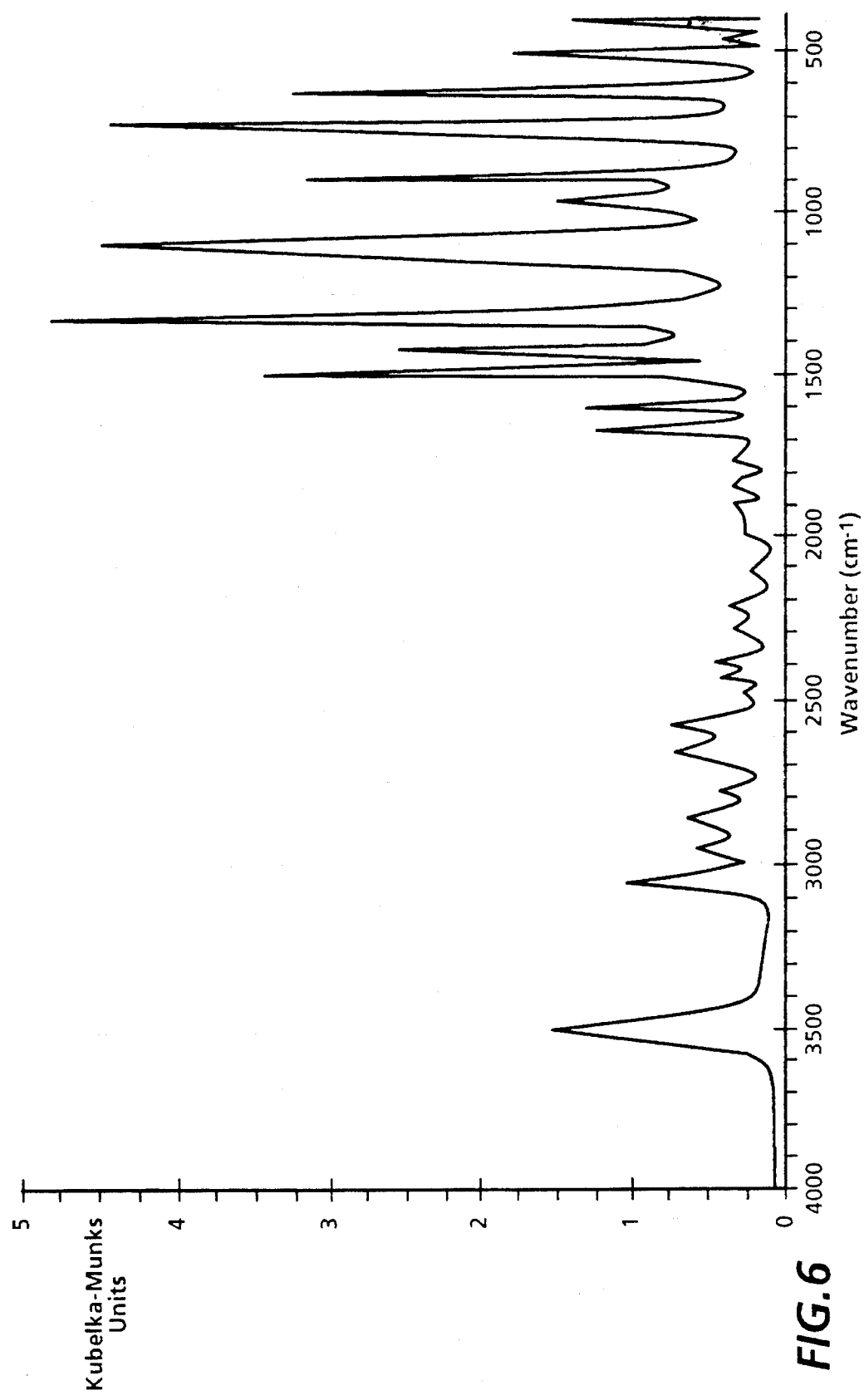
FIG. 6 represents an infrared plot of the Type V hydroxygallium phthalocyanine prepared as described in Example V.
Figure 7:
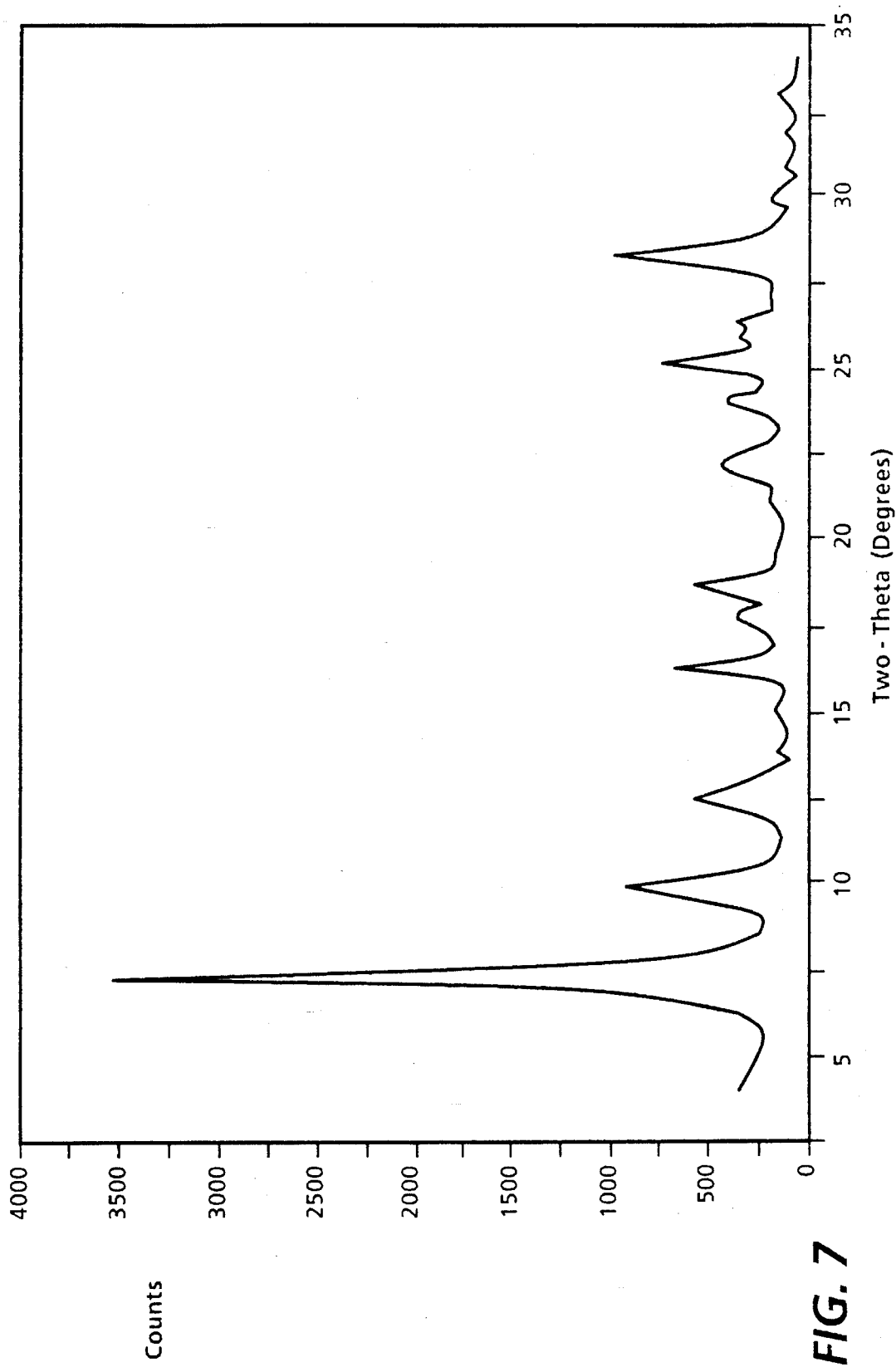
FIG. 7 represents an X-ray powder diffraction trace for the Type V hydroxygallium phthalocyanine prepared as described in Example V.

Conversion to Type V Hydroxygallium Phthalocyanine:

The Type I hydroxygallium phthalocyanine pigment obtained in Example III above was converted to Type V HOGaPc as follows. The pigment (3.0 grams) was added to 45 milliliters of N,N-dimethylformamide in a 120 milliliter glass bottle containing 90 grams of glass beads (0.25 inch in diameter). The bottle was sealed and placed on a ball mill for 24 hours. The solid resulting was isolated by filtration through a porcelain funnel fitted with a Whatman GF/F grade glass fiber filter, and washed in the filter using several 50 milliliter portions of butyl acetate. The filtercake was oven dried overnight at 50° C. to provide 2.8 grams of Type V HOGaPc which was identified by infrared spectroscopy and X-ray powder diffraction. Infrared spectroscopy major peaks at 507, 571, 631, 733, 756, 773, 897, 965, 1067, 1084, 1121, 1146, 1165, 1291, 1337, 1425, 1468, 1503, 1588, 1609, 1757, 1848, 1925, 2099, 2205, 2276, 2384, 2425, 2572, 2613, 2653, 2780, 2861, 2909, 2956, 3057 and 3499 (broad) cm$^{-1}$ (FIG. 6); X-ray diffraction pattern peaks at Bragg angles of 7.4, 9.8, 12.4, 12.9, 16.2, 18.4, 21.9, 23.9, 25.0 and 28.1, with the highest peak at 7.4 degrees 2Θ (2 theta ±0.2°) (FIG. 7).

EXAMPLE VI

Large Scale Conversion to Type V Hydroxygailium Phthalocyanine

The Type I hydroxygallium phthalocyanine pigment obtained in Example IV was converted to Type V HOGaPc in the following manner. Dry, clean ¼ inch glass beads (21 kilograms) were charged into a 20 liter polypropylene carbon and then 1.05 kilogram of the phthalocyanine was added, followed by 8.0 kilograms of DMF (dimethylformamide). The material was wet milled for 24 hours using a roll mill at a carboy rotational speed of 60 rpm, during which time a conversion to Type V HOGaPc takes place. At the end of the wet milling, the phthalocyanine was washed free of DMF in a plastic filter fitted with an air driven agitator. The HOGaPc slurry was transferred from the carboy to the filter and most of the DMF was removed by vacuum filtration. The glass beads were rinsed three times with 5 kilograms of acetone, and each wash was transferred to the filter. When most of the first acetone washes had been removed, the filtercake was rinsed twice with 20 kilograms of fresh acetone. The vacuum filtration was continued until the filtercake became very firm. The HOGaPc was then transferred to a vacuum shelf dryer and dried at 60° C. under full vacuum for 24 hours. The yield was 1.0 kilogram (95 percent) of Type V HOGaPe which was identified by infrared spectroscopy and X-ray powder diffraction. Infrared spectroscopy major peaks at 507, 571, 631, 733, 756, 773, 897, 965, 1067, 1084, 1121, 1146, 1165, 1291, 1337, 1425, 1468, 1503, 1588, 1609, 1757, 1848, 1925, 2099, 2205, 2276, 2384, 2425, 2572, 2613, 2653, 2780, 2861, 2909, 2956, 3057 and 3499 (broad) cm$^{-1}$ (identical to FIG. 6); X-ray diffraction pattern peaks at Bragg angles of 7.4, 9.8, 12.4, 12.9, 16.2, 18.4, 21.9, 23.9, 25.0 and 28.1, with the highest peak at 7.4 degrees 2Θ (2 theta ±0.2°) (identical to FIG. 7).

Comparative Example 1

Type V Hydroxygallium Phthalocyanine From Alkoxy-bridged Gallium Phthalocyanine Dimer Obtained Using Commercial Gallium Methoxide A sample of Type I hydroxygallium phthalocyanine obtained by the hydrolysis of an alkoxy-bridged gallium phthalocyanine dimer, which was synthesized by reacting gallium methoxide (obtained from a vendor) with ortho-phthalodinitrile and ethylene glycol, was converted to Type V HOGaPc by an identical procedure to that described in Example V. The Type V HOGaPc was identified by infrared spectroscopy and X-ray powder diffraction. Infrared spectroscopy major peaks at 507, 571, 631, 733, 756, 773, 897, 965, 1067, 1084, 1121, 1146, 1165, 1291, 1337, 1425, 1468, 1503, 1588, 1609, 1757, 1848, 1925, 2099, 2205, 2276, 2384, 2425, 2572, 2613, 2653, 2780, 2861, 2909, 2956, 3057 and 3499 (broad) cm-$^{-1}$ (identical to FIG. 6); X-ray diffraction pattern peaks at Bragg angles of 7.4, 9.8, 12.4, 12.9, 16.2, 18.4, 21.9, 23.9, 25.0 and 28.1, with the highest peak at 7.4 degrees 2Θ (2 theta ±0.2°) (identical to FIG. 7).

Comparative Example 2

Figure 8:
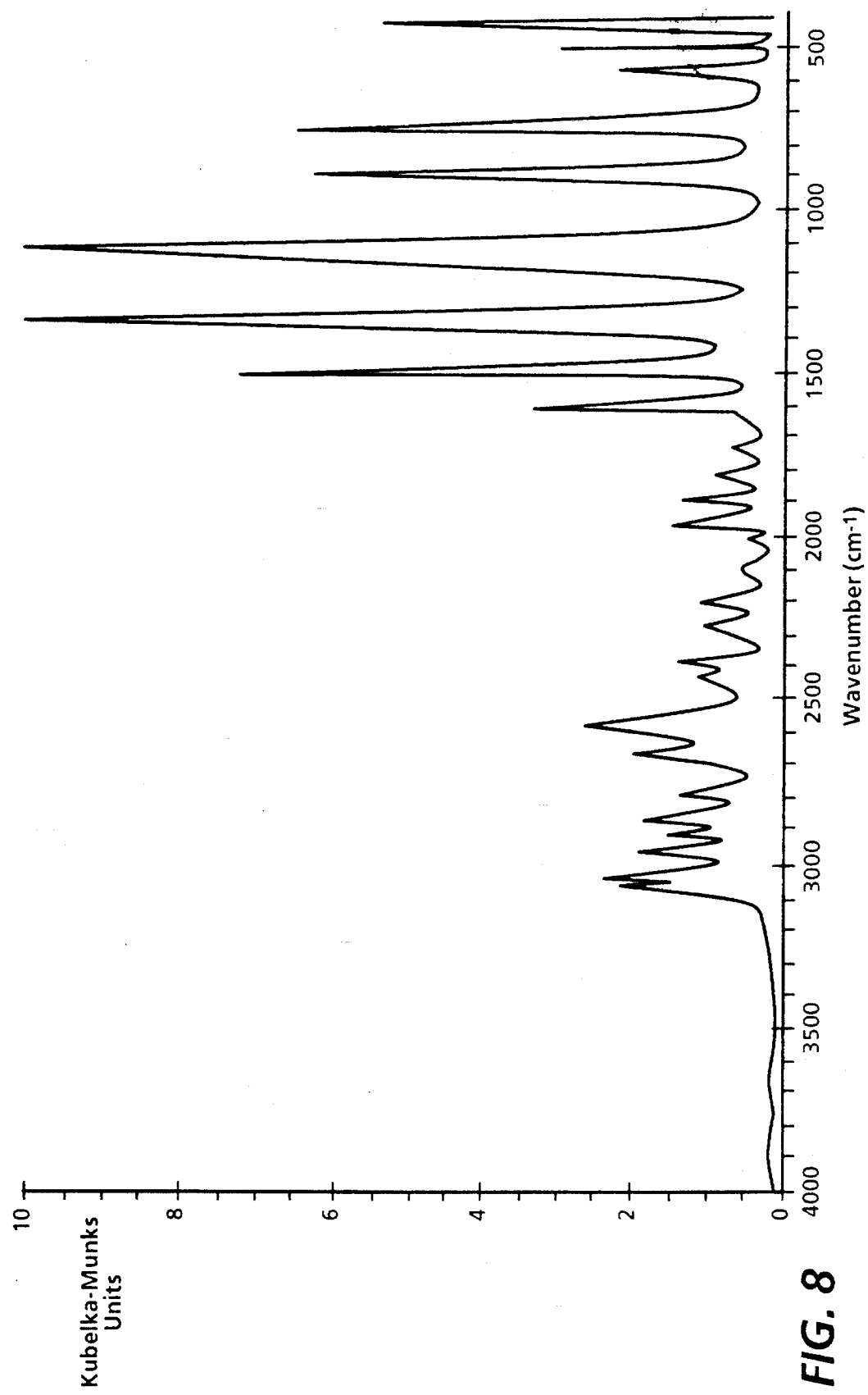
FIG. 8 represents an infrared plot of the chlorogallium phthalocyanine prepared as described in Comparative Example II.
Figure 9:
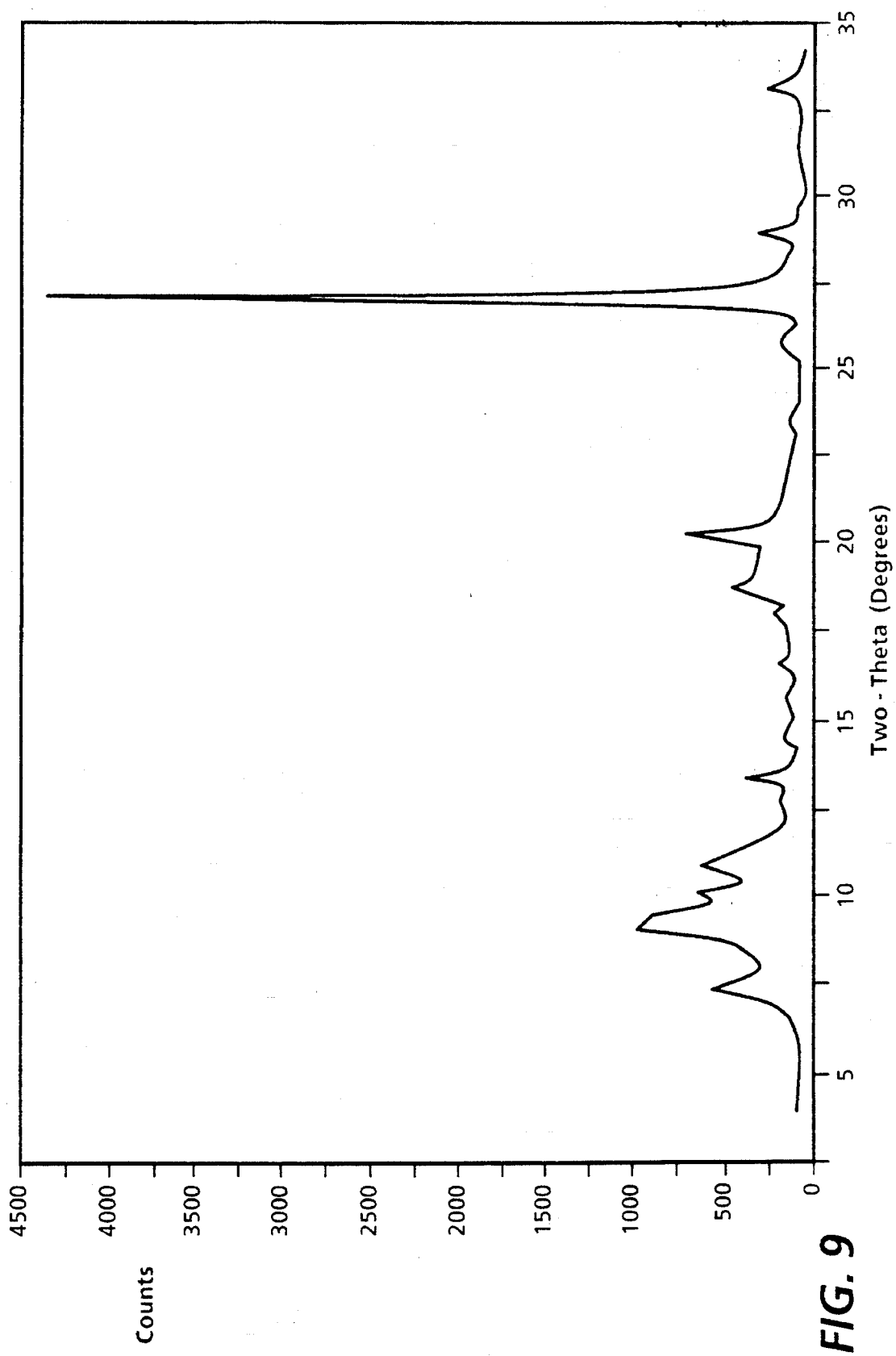
FIG. 9 represents an X-ray powder diffraction trace for the chlorogallium phthalocyanine (Type polymorph) prepared as described in Comparative Example II.

Chlorogallium Phthalocyanine Synthesis Using Gallium Trichloride in 1-Chloronaphthalene To a 5 liter round bottomed flask equipped with stirring and a nitrogen purge atmosphere were added 200 grams of $GaCl_3$ plus 582 grams of o-phthalodinitrile and 2.75 liters of 1-chloronaphthalene. The phthalocyanine synthesis was performed at 200° C. for 4 hours. The phthalocyanine was filtered at 120° C. and then washed in the filter with 350 milliliters of DMF. The product was then washed in a beaker with 1.5 liters of DMF at 22° C. for 30 minutes and filtered. The product was then washed in a beaker with 1.5 liters of DMF at 100° C. for 1 hour and filtered. The product was then washed again at 22° C. for 30 minutes in a beaker with 1.5 liters of DMF and filtered. The product was then washed in a beaker with 1.5 liters of methanol at 65° C. for 1 hour and filtered. The product was then washed again at 22° C. for 30 minutes in a beaker with 1.5 liters of methanol and filtered. The wet cake was dried at 60° C. under vacuum for 18 hours resulting in 271 grams of chlorogallium phthalocyanine (39 percent yield). The product pigment chlorogallium phthalocyanine Type V was characterized by elemental analysis, infrared spectroscopy and X-ray powder diffraction. Elemental analysis showed the presence of 5.60 percent chlorine (theoretical value for ClGaPc is 5.74 percent). Infrared spectroscopy major peaks at 432, 507, 573, 638, 718, 754, 779, 866, 897, 947, 995, 1067, 1088, 1125, 1169, 1288, 1339, 1424, 1468, 1484, 1507, 1589, 1607, 1638, 1680, 1732, 1810, 1848, 1891, 1929, 1967, 2197, 2237, 2269, 2388, 2426, 2577, 2612, 2652, 2783, 2824, 2861, 2914, 2857, 3013, 3030, 3053 and 3084 cm$^{-1}$ (FIG. 8); X-ray diffraction pattern peaks at Bragg angles of 7.3, 9.1, 10.9, 13.4, 18.6, 20.3, 27.0, 28.8 and 33.1, with the highest peak at 27.0 degrees 2Θ (2 theta ±0.2°) (FIG. 9).

Comparative Example 3

Hydrolysis of Chlorogallium Phthalocyanine to Hydroxygallium Phthalocyanine:

The hydrolysis of chlorogallium phthalocyanine synthesized in Comparative Example 2 above to hydroxygallium phthalocyanine was performed as follows. Sulfuric acid (94 to 96 percent, 125 grams) was heated to 40° C. in a 125 milliliter Edenmeyer flask and then 5 grams of the chlorogallium phthalocyanine were added. Addition of the solid was completed in about 15 minutes, during which time the temperature of the solution increased to about 48° C. The acid solution was then stirred for 2 hours at 40° C., after which it was added in a dropwise fashion to a mixture comprised of concentrated (~30 percent) ammonium hydroxide (265 milliliters) and aleionized water (435 milliliters), which had been cooled to a temperature below 5° C. Addition of the dissolved phthalocyanine was completed over the course of approximately 30 minutes, during which time the temperature of the solution increased to about 40° C. The reprecipitated phthalocyanine was then removed from the cooling bath and allowed to stir at room temperature for 1 hour. It was then filtered through a porcelain funnel fitted with a Whatman 934-AH grade glass fiber filter. The resulting blue solid was redispersed in fresh deionized water by stirring at room temperature for 1 hour and filtered as before. This process was repeated at least three times until the conductivity of the filtrate was <20 μS. The filtercake was oven dried overnight at 50° C. to give 4.75 grams (95 percent) of Type 1HOGaPc, identified by infrared spectroscopy and X-ray powder diffraction. Infrared spectroscopy major peaks at 507, 573, 629, 729, 756, 772, 874, 898, 956, 984, 1092, 1121, 1165, 1188, 1290, 1339, 1424, 1468, 1503, 1588, 1611, 1757, 1835, 1951, 2099, 2207, 2280, 2384, 2425, 2570, 2608, 2652, 2780, 2819, 2853, 2907, 2951, 3049 and 3479 (broad) cm$^{-1}$ (identical to FIG. 4); X-ray diffraction pattern peaks at Bragg angles of 6.8, 13.0, 16.5, 21.0, 26.3 and 29.5, with the highest peak at 6.8 degrees 2Θ (2 theta ±0.2°) (identical to FIG. 5).

Comparative Example 4

Conversion to Type V Hydroxygallium Phthalocyanine

The Type 1hydroxygallium phthalocyanine pigment obtained in Comparative Example 3 above was converted to Type V HOGaPc as follows. The Type I hydroxygallium phthalocyanine pigment (3.0 grams) was added to 25 milliliters of N,N-dimethylformamide in a 60 milliliter glass bottle containing 60 grams of glass beads (0.25 inch in diameter). The bottle was sealed and placed on a ball mill overnight (18 hours). The solid was isolated by filtration through a porcelain funnel fitted with a Whatman GF/F grade glass fiber filter, and washed in the filter using several 25 milliliter portions of acetone. The filtercake was oven dried overnight at 50° C. to provide 2.8 grams of Type V HOGaPc which was identified by infrared spectroscopy and X-ray powder diffraction. Infrared spectroscopy major peaks at 507, 571, 631, 733, 756, 773, 897, 965, 1067, 1084, 1121, 1146, 1165, 1291, 1337, 1425, 1468, 1503, 1588, 1609, 1757, 1848, 1925, 2099, 2205, 2276, 2384, 2425, 2572, 2613, 2653, 2780, 2861, 2909, 2956, 3057 and 3499 (broad) cm.$^{-1}$ (identical to FIG. 6); X-ray diffraction pattern peaks at Bragg angles of 7.4, 9.8, 12.4, 12.9, 16.2, 18.4, 21.9, 23.9, 25.0 and 28.1, with the highest peak at 7.4 degrees 2Θ (2 theta ±0.2°) (identical to FIG. 7).

EXAMPLE VII

The Type V hydroxygallium phthalocyanine prepared in Examples V and VI, and Comparative Examples 1 and 4 above can be selected as a photogenerating layer in a layered photoconductive imaging member prepared by the following procedure. An aluminized MYLAR® substrate, about 4 mil in thickness, was first coated with a silane/zirconium alkoxide solution prepared by mixing 6.5 grams of acetylacetonate tributoxy zirconium (ZC540), 0.75 gram of (aminopropyl) trimethoxysilane (A 1110), 28.5 grams of isopropyl alcohol, and 14.25 grams of butanol using a number 5 wire wound rod applicator. The blocking layer so formed was dried at 140° C. for 20 minutes; the final thickness was measured to be 0.1 micron.

A dispersion was prepared by combining 0.5 gram of the HOGaPc prepared as described in Example r, and 0.26 gram of poly(vinyl butyral) in 25.2 grams of chlorobenzene in a 60 milliliter glass jar containing 70 grams of 0.8 millimeter glass beads. The dispersion was shaken on a paint shaker for 2 hours and then coated onto the silane/zirconium layer described above using a number 6 wire wound rod applicator. The Type V HOGaPc photogenerating layer formed was dried at 100° C. for 10 minutes to a final thickness of about 0.20 micron.

A hole transporting layer solution was prepared by dissolving 5.4 grams of N,N'-diphenyl-N,N-bis(3-methylphenyl)-1,1'-biphenyl-4,4'-diamine, and 8.1 grams of polycarbonate in 61.5 grams of chlorobenzene. The solution was coated onto the Type V HOGaPc generator layer using a 10 mil film applicator. The charge transporting layer thus obtained was dried at 115° C. for 60 minutes to provide a final thickness of about 28 microns.

The xerographic electrical properties of photoresponsive imaging members prepared as described above were determined by electrostatically charging the surface thereof with a corona discharge source until the surface potential, as measured by a capacitatively coupled probe attached to an electrometer, attained an initial dark value, $V_0$, of −800 volts. After resting for 0.5 second in the dark, the charged member reached a surface potential, $V_{ddp}$, or dark development potential. The member was then exposed to filtered light from a Xenon lamp. A reduction in surface potential from $V_{ddp}$ to a background potential, $V_{bg}$, due to the photodischarge effect was observed. The dark decay in volts per second was calculated as $(V_0-V_{ddp})/0.5$. The half exposure energy, that is $E_{1/2}$, is the amount of exposure energy causing reduction of the $V_{ddp}$ to half of its initial value, was determined. $E_{800-100V}$, which is the amount of exposure energy causing reduction of the $V_{ddp}$ from −800 volts to −100 volts, was also determined. The wavelength of light selected was 780 nanometers.

In a cycling test, devices were charged with a corotron to about −800 volts. They were exposed with 775 nanometers of light with an intensity of about 7 ergs/cm² and erased with white light of about 60 ergs/cm². The dark development ($V_{ddp}$) and background ($V_{bg}$) potentials were measured and recorded while the testing was performed for 10,000 cycles. After the cycling test had been completed, the devices remained in the dark for about 20 hours. After charging the device to about −800 volts with a corotron, they were exposed with 775 nanometers of light with an intensity of 3 ergs/cm² and erased with white light of about 200 ergs/cm². The dark development and background potentials were measured and recorded while the testing was performed for 5,000 cycles. The significantly higher erase light intensity used in this second test compared to the standard test accelerates the cycledown (decrease in the dark development potential) in the photogenerator material and is thus considered a stress test.

The imaging member (Device 1) prepared with Type V hydroxygallium phthalocyanine prepared in Example V had a dark decay of 6.0 volts per second, $E_{1/2}=1.61$ ergs/cm², and an $E_{800-100\,V}=4.02$ ergs/cm². In cycling tests, Device 1 had a cycle down of −25 volts after 10,000 cycles and a cycledown of −29 volts after 5,000 cycles in the more stressful test.

The imaging member (Device 2) containing Type V hydroxygallium phthalocyanine of Example VI had a dark decay of 9.6 volts per second, $E_{1/2}=1.57$ ergs/cm², and an $E_{800-100V}=3.60$ ergs/cm². In cycling tests, Device 2 had a cycle down of −27 volts after 10,000 cycles and a cycledown of −33 volts after 5,000 cycles in the more stressful test.

The imaging member (Device 3) containing Type V hydroxygallium phthalocyanine of Comparative Example 1 had a dark decay of 19.8 volts per second, $E_{1/2}=1.47$ ergs/cm², and an $E_{800-100V}=3.19$ ergs/cm². In cycling tests, Device 3 had a cycledown of −26 volts after 10,000 cycles and a cycledown of −48 volts after 5,000 cycles in the more stressful test.

The imaging member (Device 4) containing Type hydroxygailium phthalocyanine of Comparative Example 4 had a dark decay of 22.2 volts per second, $E_{1/2}=1.54$ ergs/cm², and an $E_{800-100V}=3.84$ ergs/cm². In cycling tests, Device 3 had a cycledown of −47 volts after 10,000 cycles and a cycledown of −90 volts after 5,000 cycles in the more stressful test.

Table 1 that follows summarizes the information and data for layered imaging members identified as Devices 1, 2, 3 and 4, which members are comprised of the components illustrated in the Examples described herein. Devices 1, 2, 3 and 4 are thus comprised of equivalent components for the data presented, except that the Type hydroxygallium phthalocyanines (Type V HOGaPc) obtained from the Examples V and VI and Comparative Examples 1 and 4 were selected. The Type V hydroxygallium phthalocyanines of the Examples V and VI were prepared according to the processes of the present invention by the synthesis of the alkoxy-bridged gallium phthalocyanine dimer precursors as described in Examples I and II, respectively; the preparation of the Type I hydroxygallium phthalocyanines from the alkoxy-bridged gallium phthalocyanine dimers as described in Examples III and IV, respectively; and by conversion of the Type I hydroxygallium phthalocyanines to Type V hydroxygailium phthalocyanines as described in Examples V and IV, respectively. The Type V hydroxygallium phthalocyanine of the Comparative Example 1 was prepared according to a process similar to the present invention by the synthesis of an alkoxy-bridged gallium phthalocyanine dimer precursor using commercially supplied gallium methoxide; the preparation of the Type I hydroxygallium phthalocyanine from the alkoxy-bridged gallium phthalocyanine dimer; and conversion of the Type I hydroxygallium phthalocyanine to Type V hydroxygallium phthalocyanine as described in Comparative Example 1. The Type V hydroxygallium phthalocyanine of the Comparative Example 4 was prepared according to a process of the previous art by the synthesis of a chlorogallium phthalocyanine precursor (ClGaPc) as described in Comparative Example 2; the preparation of the Type I hydroxygailium phthalocyanine from chlorogallium phthalocyanine as described in Comparative Example 3; and conversion of the Type I hydroxygallium phthalocyanine to Type V hydroxygallium phthalocyanine as described in Comparative Example 4.

TABLE 1

Comparative Electrical Properties of Type V HOGaPc

| Device # | HOGaPc Precursor | Source of Type V HOGaPc | Dark Decay Volts/Sec. | $E_{1/2}$ erg/cm² | $E_{800-100V}$ erg/cm² | Cycle-Down 10k Volts | Cycle-Down 5k Stress Test Volts |
|---|---|---|---|---|---|---|---|
| 1 | Dimer | Example V | 6.0 | 1.61 | 4.02 | −25 | −29 |
| 2 | Dimer | Example VI | 9.6 | 1.57 | 3.60 | −27 | −33 |
| 3 | Dimer | Compara- | 19.8 | 1.47 | 3.19 | −26 | −48 |

TABLE 1-continued

Comparative Electrical Properties of Type V HOGaPc

| Device # | HOGaPc Precursor | Source of Type V HOGaPc | Dark Decay Volts/ Sec. | $E_{1/2}$ erg/cm$^2$ | $E_{800-100V}$ erg/cm$^2$ | Cycle-Down 10k Volts | Cycle-Down 5k Stress Test Volts |
|---|---|---|---|---|---|---|---|
| 4 | [commercial Ga(OMe)$_3$] ClGaPc | tive Example 1 Comparative Example 4 | 22.2 | 1.54 | 3.84 | −47 | −90 |

From the information summarized in Table 1, it is evident that the Type V hydroxygallium phthalocyanine obtained from the dimer precursor synthesized by the in situ route, according to the processes of this invention, enables improved (reduced) dark decay and better cyclic stability (smaller voltage loss) to imaging members, when compared to Type V hydroxygallium phthalocyanine obtained from either a chlorogallium phthalocyanine precursor, or a dimer precursor synthesized using commercial gallium methoxide.

Thus, with the imaging members containing the Type V prepared by the invention process, there was obtained in embodiments a more electrically stable imaging permitting improved copy quality for developed images after repeated use.

Other embodiments and modifications of the present invention may occur to those skilled in the art subsequent to a review of the information presented herein; these embodiments and modifications, as well as equivalents thereof, are also included within the scope of this invention.

What is claimed is:

1. A process for the preparation of Type V hydroxygallium phthalocyanine consisting essentially of the in situ formation of an alkoxy-bridged gallium phthalocyanine dimer, hydrolyzing said alkoxy-bridged gallium phthalocyanine dimer to hydroxygallium phthalocyanine, and subsequently converting the hydroxygallium phthalocyanine product obtained to Type V hydroxygallium phthalocyanine.

2. A process in accordance with claim 1 wherein the phthalocyanine dimer is of the formula $C_{32}H_{16}N_8GaOROGaN_8H_{16}C_{32}$ wherein R is an alkyl group or an alkyl ether group, and wherein said dimer is hydrolyzed to hydroxy gallium phthalocyanine, and the hydroxygallium phthalocyanine product obtained is converted to Type V hydroxygallium phthalocyanine by a solvent treatment.

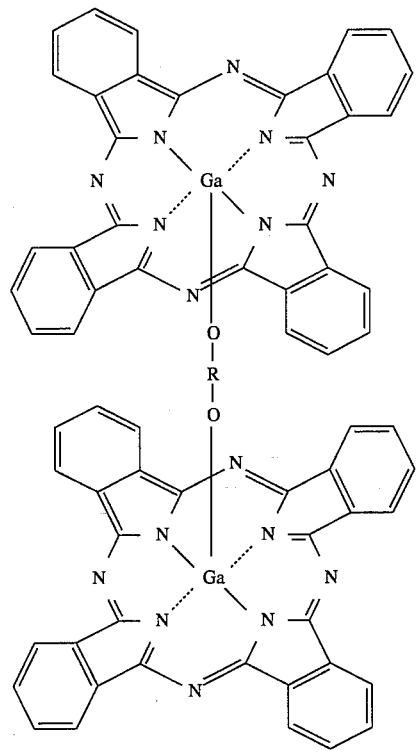

3. A process in accordance with claim 1 wherein the phthalocyanine dimer is $C_{32}H_{16}N_8GaOCH_2CH_2OGaN_8H_{16}C_{32}$, 1,2-di(oxogallium phthalocyaninyl) ethane, $C_{32}H_{16}N8GaOCH_2CH(CH_3)OGaN_8H_{16}C_{32}$, 1,2-di(oxogallium phthalocyaninyl) propane, $C_{32}H_{16}N_8GaOCH_2CH_2CH_2OGaN_8H_{16}C_{32}$, 1,3-di(oxogallium phthalocyaninyl) propane, or $C_{32}H_{16}N_8GaOCH_2CH_2CH_2CH_2OGaN_8H_{16}C_{32}$, 1,4-di(oxogallium phthalocyaninyl) butane.

4. A process in accordance with claim 1 wherein said dimer is obtained by the reaction of gallium trichloride with an alkali metal alkoxide in a solvent, reacting the resulting mixture of gallium alkoxide, alkali metal halide byproduct and solvent with orthophthalodinitrile or 1,3-diiminoisoindoline, and 8 diol; and wherein said, diol is selected from the group consisting of ethylene glycol, 1,3-propanediol, 2-methyl-1,3-propanediol, 2,2-dimethyl-1,3-propanediol, 1,3-butanediol, 2,3-butanediol, 1,4-butanediol, 1,4-cyclohexanediol and 1,6-hexanediol.

5. A process in accordance with claim 4 wherein the diol is ethylene glycol.

6. A process in accordance with claim 4 wherein the diol contains additional hydroxyl groups and is 1,2,3-propanetriol (glycerol) or 1,2,4-butanetriol.

7. A process in accordance with claim 4 wherein the diol is an ether with from 4 to about 10 carbon atoms.

8. A process in accordance with claim 4 wherein the diol is the ether diethylene glycol or triethylene glycol.

9. A process in accordance with claim 4 wherein the diol is ethylene glycol.

10. A process in accordance with claim 1 wherein hydrolysis comprises dissolving the alkoxy-bridged gallium phthalocyanine dimer in a strong acid by stirring, at a temperature of from about 0° C. to about 100° C., and then precipitating hydroxygallium phthalocyanine by adding the resulting solution to water, or to a basic aqueous solution.

11. A process in accordance with claim 10 wherein the strong acid is sulfuric acid of a concentration of 90 to about 99 percent.

12. A process in accordance with claim 11 wherein the weight ratio of sulfuric acid to alkoxy-bridged gallium phthalocyanine dimer is from 10 to 1 to 100 to 1.

13. A process in accordance with claim 10 wherein the basic aqueous solution contains an organic or inorganic base in sufficient amount to assure a final pH of 7 to 12 after the completion of the precipitation step.

14. A process in accordance with claim 13 wherein the base is ammonium hydroxide.

15. A process in accordance with claim 2 wherein the conversion by solvent treatment comprises milling the hydroxygallium phthalocyanine in said solvent for a period of about 1 minute to 48 hours, followed by filtering and washing to isolate Type V hydroxygallium phthalocyanine.

16. A process in accordance with claim 1 wherein said converting is accomplished by solvent treatment, which treatment comprises stirring hydroxygallium phthalocyanine Type I in said solvent for a period of about 5 minutes to 48 hours, followed by filtering and washing to isolate Type V hydroxygallium phthalocyanine.

17. A process in accordance with claim 16 wherein the conversion by solvent treatment is accomplished at a temperature of from about 0° C. to about 50° C., and preferably at about 25° C. for a period of from about 1 hour to about 24 hours.

18. A process in accordance with claim 1 wherein the conversion is accomplished by solvent treatment and wherein the solvent selected for the conversion is N,N-dimethylformamide quinoline, 1-chloronaphthalene, N-methylpyrrotidone (1-methyl-2-pyrrolidinone), dimethylsulfoxide, or pyridine.

19. A process in accordance with claim 18 wherein the solvent is N,N-dimethylformamide selected in an amount of from about 5 volume parts to about 50 volume parts, and preferably about 15 to about 25 volume parts for each weight part of hydroxygallium phthalocyanine that is selected.

20. A process in accordance with claim 1 wherein the Type V hydroxygallium phthalocyanine obtained is washed with N,N-dimethylformamide.

21. A process in accordance with claim 1 wherein the Type V hydroxygallium phthalocyanine obtained is washed with an organic solvent of acetone, methylethylketone, ethyl acetate or butyl acetate.

22. A process in accordance with claim 1 wherein the Type V hydroxygallium phthalocyanine obtained is washed with deionized water.

23. A process in accordance with claim 2 wherein the organic solvent treatment is accomplished by milling with glass, ceramic or metallic beads from about 1 millimeter to about 30 millimeters in diameter, and preferably about 1 to about 6 millimeters in diameter.

24. A process in accordance with claim 23 wherein the organic solvent treatment by milling is accomplished in a roll mill, jar mill, vibration mill, or an attritor.

25. A process in accordance with claim 1 wherein the Type V hydroxygailium phthalocyanine obtained has an X-ray diffraction pattern with major peaks at Bragg angles of 7.4, 9.8, 12.4, 12.9, 16.2, 18.4, 21.9, 23.9, 25.0, 28.1, and the highest peak at 7.4 degrees 2Θ (2 theta ±0.2°).

26. A process in accordance with claim 1 wherein the Type V hydroxygallium phthalocyanine obtained is of small particle size of from about 0.01 μm to about 0.5 μm in average volume diameter.

27. A process for the preparation of Type V hydroxygallium phthalocyanine which comprises the formation of an alkoxy-bridged gallium phthalocyanine dimer by the reaction of a gallium alkoxide, which has been formed from reacting gallium trichloride in a solvent, with a sodium alkoxide, and selecting the resulting mixture of gallium alkoxide and sodium chloride byproduct for the reaction with ortho-phthalodinitrile or 1,3-diiminoisoindoline and a diol; hydrolyzing the resulting alkoxy-bridged gallium phthalocyanine dimer to hydroxygallium phthalocyanine; and subsequently converting the product obtained to Type V hydroxygallium phthalocyanine by a solvent treatment; and wherein said diol is selected from the group consisting of ethylene glycol, 1,3-propanediol,2-methyl-1,3-propanediol, 2,2-dimethyl-1,3-propanediol 1,3butanediol,2,3-butanediol, 1,4-butanediol,1,4-cyclohexanediol and 1,6-hexanediol.

28. A process in accordance with claim 27 wherein there is accomplished the dissolution of 1 part of gallium trichloride in about 1 part to about 100 parts, and preferably about 10 parts of an organic solvent of benzene, toluene, or xylene at a temperature of from about 0° C. to about 100° C., and preferably at a temperature of about 25° C. to form a solution of gallium trichloride; followed by the addition of 3 parts of an alkali metal alkoxide of sodium methoxide, sodium ethoxide, or sodium propoxide in a solution to provide a gallium alkoxide solution, and an alkali metal salt byproduct at a temperature of from about 0° C. to about 100° C., and preferably at a temperature of about 20° C. to about 40° C, followed by the reaction thereof with from about 1 part to about 10 parts, and preferably about 4 parts of ortho-phthalodinitrile or 1,3-diiminoisoindoline, and a diol in an amount of from about 3 parts to about 100 parts, and preferably about 10 parts for each part of the gallium trichloride selected at a temperature of from about 150° C. to about 220° C., and preferably at a temperature of 195° C. for a period of 30 minutes to 6 hours, and preferably about 2 hours to provide an alkoxy-bridged gallium phthalocyanine dimer; subsequently isolating the dimer by filtration at a temperature of about 20° C. to about 180° C., and preferably at about 120° C. to provide a dark blue solid product.

29. A process in accordance with claim 28 wherein the dimer isolated is subsequently washed with an organic solvent at a temperature of from about 20° C. to about 120° C., followed by washing with aqueous solvents, or water to provide a pure alkoxy-bridged gallium phthalocyanine dimer; followed by hydrolyzing said alkoxy-bridged gallium phthalocyanine dimer; subsequently contacting the resulting hydroxygallium phthalocyanine Type I with a solvent to obtain a hydroxygallium phthalocyanine Type V.

30. A process in accordance with claim 28 wherein the dimer isolated is subsequently washed with an organic solvent dimethylformamide at a temperature of from about 20° C. to about 120° C., and preferably at a temperature of about 80° C., followed by washing with aqueous solvents of ammonium hydroxide, or sodium hydroxide, or cold or hot water to provide a pure alkoxy-bridged gallium phthalocyanine dimer in a high yield based upon the amount of gallium trichloride selected; followed by hydrolyzing said alkoxy-bridged gallium phthalocyanine dimer by acid pasting, whereby the phthalocyanine dimer is dissolved in concentrated sulfuric acid and then reprecipitated in a solvent of water, or a dilute ammonia solution, from about 10 to about 15 percent; and subsequently treating the resulting hydroxygallium phthalocyanine Type I with a solvent of N,N-dimethylformamide present in an amount of from about 1 volume part to about 50 volume parts, and preferably about 15 volume parts, for each weight part of hydroxygallium phthalocyanine that is selected, which treatment is accomplished by ball milling said Type I hydroxygallium phthalocyanine pigment in the presence of spherical glass beads of from about 1 millimeter to about 6 millimeters in diameter at room temperature, about 25° C., for a period of from about 12 hours to about 1 week, and preferably about 24 hours, and wherein there is obtained hydroxygallium phthalocyanine Type V.

31. A process in accordance with claim 30 wherein the purity of said hydroxygallium phthalocyanine Type V is from about 75 to about 99 percent, and the yield is from about 70 to about 80 percent.

32. A process in accordance with claim 4 wherein the diol is 1,2-ethanediol (ethylene glycol), 1,2-propanediol (propylene glycol), 1,2-butanediol (butylene glycol), 1,2-hexanediol or 1,2-cyclohexanediol.

33. A process for the preparation of an alkoxy-bridged gallium phthalocyanine dimer by the reaction of gallium trichloride with an alkali metal alkoxide in a solvent; thereafter removing the alkali metal halide byproduct formed; and reacting the obtained gallium alkoxide solution with ortho-phthalodinitrile or 1,3-diiminoisoindoline, and a diol.

34. A process in accordance with claim 30 wherein the purity of said hydroxygallium phthalocyanine Type V is from 99.0 to 99.99 percent.

* * * * *